(12) United States Patent
Aoki et al.

(10) Patent No.: US 11,969,372 B2
(45) Date of Patent: Apr. 30, 2024

(54) KNEE BRACE AND LEG BRACE

(71) Applicant: Toyota Jidosha Kabushiki Kaisha, Toyota (JP)

(72) Inventors: Eisuke Aoki, Toyota (JP); Takahiro Takeda, Toyota (JP); Tomio Ikeda, Toyota (JP); Tadashi Odashima, Toyota (JP)

(73) Assignee: TOYOTA JIDOSHA KABUSHIKI KAISHA, Toyota Aichi-ken (JP)

( * ) Notice: Subject to any disclaimer, the term of this patent is extended or adjusted under 35 U.S.C. 154(b) by 115 days.

(21) Appl. No.: 17/177,777

(22) Filed: Feb. 17, 2021

(65) Prior Publication Data

US 2021/0259869 A1     Aug. 26, 2021

(30) Foreign Application Priority Data

Feb. 21, 2020    (JP) ................. 2020-028534

(51) Int. Cl.
*A61F 5/01*         (2006.01)

(52) U.S. Cl.
CPC .... *A61F 5/0123* (2013.01); *A61F 2005/0137* (2013.01); *A61F 2005/0148* (2013.01)

(58) Field of Classification Search
CPC ...... A61F 5/0109; A61F 5/0123; A61F 5/013; A61F 5/0125; A61F 5/32; A61F 5/01; A61F 5/26; A61F 5/30; A61F 5/0106; A61F 5/0102; A61F 2005/0137; A61F 2005/0144; A61F 2005/0179; A61F 2005/0197; A61F 2005/0151; A61F 2005/0172; A61F 2005/0148; A61F 2005/0165; A61F 2005/0139; A61F 2005/0176; A61F 2005/0167; A61F 2005/0181; A61F 2005/0174; A61F 2/64; A61F 2/642; A61F 2/646; A61F 5/05858; A61F 5/3753; A61F 5/0118; A61F 5/37387; A61F 5/3715; A61F 5/37; A61F 5/373; A61F 2005/0158; A61F 2005/0132; A61F 2005/0153; A61B 5/70; A61H 1/02; A61H 1/0274; A61H 1/0277;

(Continued)

(56) References Cited

U.S. PATENT DOCUMENTS 4,723,539 A    2/1988   Townsend
5,611,774 A *   3/1997   Postelmans ........... A61F 5/0123
                                                           602/26

(Continued)

FOREIGN PATENT DOCUMENTS

EP        0173161 A1    3/1986
JP        5185458 B1    4/2013
JP        5189714 B2    4/2013

*Primary Examiner* — Alireza Nia
*Assistant Examiner* — Daniel A Miller
(74) *Attorney, Agent, or Firm* — Dinsmore & Shohl LLP

(57) ABSTRACT

A knee brace includes a thigh fixing part, a shank fixing part, an outer leg joint that couples the thigh fixing part with the shank fixing part, and an inner leg joint that couples the thigh fixing part with the shank fixing part. When the wearer P flexes his/her knee joint, a lower arm is rotated with respect to an upper arm along with a rotation fulcrum shaft sliding in a long groove and a cam shaft sliding in a cam groove. When the outer leg joint and the inner leg joint are extended, the lower arm of the outer leg joint is configured to be moved relatively forward with respect to the lower arm of the inner leg joint.

8 Claims, 21 Drawing Sheets

(58) Field of Classification Search
CPC .......... A61H 1/0281; A61H 2201/0173; A61H 2201/1614; A61H 2201/1635; A61H 2201/0135; A61G 7/05; A61G 7/075; A61G 7/0755; A61G 7/065; A61G 13/1235; A61G 13/1255; A61G 13/10; A61G 13/12; Y10T 16/54028; Y10T 403/32196; E05D 11/1028
USPC ....... 602/16, 20, 23, 26; 623/39–44; 16/221, 16/357–359, 366
See application file for complete search history.

(56) References Cited

U.S. PATENT DOCUMENTS

| | | | |
|---|---|---|---|
| 2006/0089581 A1* | 4/2006 | Lambert | A61F 5/0123 602/26 |
| 2013/0289458 A1* | 10/2013 | Okada | A61F 5/0102 602/16 |
| 2019/0091055 A1* | 3/2019 | Best | A61F 5/0123 |

* cited by examiner

KNEE BRACE AND LEG BRACE

CROSS REFERENCE TO RELATED APPLICATIONS

This application is based upon and claims the benefit of priority from Japanese patent application No. 2020-28534, filed on Feb. 21, 2020, the disclosure of which is incorporated herein in its entirety by reference.

BACKGROUND

The present disclosure relates to a knee brace and a leg brace.

As a typical example of a symptom accompanied by a pain in a knee joint, knee osteoarthritis is known. Knee osteoarthritis is a case in which a function of a knee joint is impaired by muscle weakness, aging, obesity, and the like, causing wear of knee cartilage, loose engagement of meniscus, deformity, rupture, excessive congestion of synovial fluid due to inflammation, and causes a pain when walking.

An advancement of the knee osteoarthritis may cause a varus deformity due to joint destruction, resulting in bowleg which is commonly called O-leg. Bowleg is believed to be a cause of the knee osteoarthritis along with knock-knee, which is commonly called X-leg, intimately related to the knee osteoarthritis.

In the case of bowleg, a cartilage inside the knee joint tends to be damaged. As the state of the knee osteoarthritis advances accompanied by bowleg, leg curvature becomes severer to make an inclination of the shank still steeper, further wearing the joint cartilage. When bones rub each other directly due to the wear of the cartilage, a strong pain is felt disabling a walk.

To treat the knee osteoarthritis, an operative treatment of sectioning a knee joint and implanting a metallic artificial joint, and a conservative treatment of continuing rehabilitation using a gait training equipment to recall a memory of correct walking behavior, are known.

With the operative treatment, though the pain of walking is eliminated, there is a drawback that the patient can sit only on a chair due to a narrow rotation angle of the artificial joint and that the patient cannot stand up if both legs have the artificial joint. Another drawback is that the useful life is approximately 10 years because aging may weaken the bone and lose strength balance with metal and therefore a further surgery will be required after the useful life. Furthermore, the operative treatment is expensive.

On the other hand, the conservative treatment is a long-term treatment of relieving the pain while walking using a knee brace and enhancing muscles by regularly walking every day, which requires physical strength and patience of the patient, but does not present the drawbacks unique to the operative treatment.

In order to solve the aforementioned problems, Patent Literature 1 (Japanese Patent No. 5189714) discloses a knee brace capable of reproducing a screw-home movement of a healthy knee joint in the knee joint of the knee osteoarthritis patient by generating an outward twist when fully extending out the knee joint.

SUMMARY

Incidentally, one of the features of patients suffering from advanced inner-side-type knee osteoarthritis is shank over-external rotation in which the shank is shifted to an angle twisted in an external rotation direction with respect to the thigh. In the state of mal-alignment in which the shank is rotated abnormally, stress is applied to the inner side of the knee, which increases the pain. Further, it is known that the pain that patients suffering from knee osteoarthritis feel when they walk is related to an external varus moment. The external varus moment can be obtained by a product of the moment arm between the load from a foot part and the knee joint. An excessive external rotation of the lower limb when the state of the leg is in an idling leg state or a knee extending state abducts the foot part and induces a bow-legged gait. When the leg is in the standing leg state, the moment arm increases, the external varus moment increases, and a mechanical stress applied to the knee increases.

An object of the present disclosure is to solve the above problem due to the over-external rotation of the shank of the patients suffering from advanced inner side knee osteoarthritis and to provide a technique for preventing a shank from being externally rotated with respect to a thigh when the knee joint is extended.

According to an aspect of the present disclosure, a knee brace for a knee osteoarthritis patient, the knee brace including: a thigh fixing part that is attached to a thigh of a patient; a shank fixing part that is attached to a shank of the patient; an outer leg joint that couples the thigh fixing part with the shank fixing part, is arranged in an outer leg side of the knee joint of the patient, and can be flexed; and an inner leg joint that couples the thigh fixing part with the shank fixing part, is arranged in an inner leg side of the knee joint of the patient, and can be flexed, in which each of the outer leg joint and the inner leg joint includes an upper arm that is provided along a side part of the thigh and a lower arm that is provided along a side part of the shank, the upper arm and the lower arm are coupled to each other by a coupling part that is provided in a side part of the knee joint, and the lower arm of the outer leg joint is configured to be moved forward relative to the lower arm of the inner leg joint when the outer leg joint and the inner leg joint are extended is provided. According to the above configuration, the knee brace operates to internally rotate the shank with respect to the thigh when the knee joint is extended. Therefore, it is possible to prevent the shank from being externally rotated with respect to the thigh when the knee joint is extended. Further, since it is possible to prevent the shank from being externally rotated with respect to the thigh, the effect that the moment arm of the knee joint becomes small and the varus moment is reduced can be exerted as well.

The coupling part may include: a cam groove provided in the upper arm or the lower arm; a long groove provided in the lower arm or the upper arm; a rotation fulcrum shaft that is provided in the upper arm or the lower arm and is slid in the long groove; and a cam shaft that is provided in the lower arm or the upper arm and is slid in the cam groove, and when the patient flexes his/her knee joint, the lower arm may be configured to be rotated with respect to the upper arm along with the rotation fulcrum shaft sliding in the long groove and the cam shaft sliding in the cam groove.

The cam groove may be provided in the upper arm, the long groove may be provided in the lower arm, the rotation fulcrum shaft may be provided in the upper arm, and the cam shaft may be provided in the lower arm.

The long groove of the lower arm of the outer leg joint may be inclined with respect to a longitudinal direction of the lower arm in such a way that an end part of the long groove where the rotation fulcrum shaft is provided when the outer leg joint is extended is positioned behind the patient, and the long groove of the lower arm of the inner leg joint may be inclined with respect to the longitudinal direction of the lower arm in such a way that the end part of the long groove where the rotation fulcrum shaft is provided when the inner leg joint is extended is positioned in the front of the patient. According to the above configuration, a configuration of internally rotating the shank with respect to the thigh when the knee joint is extended can be obtained with the simple configuration.

When the outer leg joint and the inner leg joint are extended, a distance from the rotation fulcrum shaft of the outer leg joint to the thigh fixing part or the shank fixing part may become short and a distance from the rotation fulcrum shaft of the inner leg joint to the thigh fixing part or the shank fixing part may become long. According to the above configuration, when the knee joint is extended, the knee joint is pressed toward the inner leg side, whereby the pain due to the rubbing of the bones on the inner leg side of the knee joint can be relieved.

At a stage before the extension of the outer leg joint and the inner leg joint is completed, the distance from the rotation fulcrum shaft of the outer leg joint to the thigh fixing part or the shank fixing part may become the shortest and the distance from the rotation fulcrum shaft of the inner leg joint to the thigh fixing part or the shank fixing part may become the longest. That is, the pain due to the rubbing of the bones on the inner leg side of the knee joint appears most remarkably at the stage before the extension of the outer leg joint and the inner leg joint is completed. Therefore, according to the above configuration, the pain due to the rubbing of the bones on the inner leg side of the knee joint can be efficiently reduced.

When it is assumed that a knee joint angle when the outer leg joint and the inner leg joint are extended is 0 degrees and the knee joint angle increases in a positive direction when the outer leg joint and the inner leg joint are flexed, the distance from the rotation fulcrum shaft of the outer leg joint to the thigh fixing part or the shank fixing part may become the shortest and the distance from the rotation fulcrum shaft of the inner leg joint to the thigh fixing part or the shank fixing part may become the longest when the knee joint angle is between 20 degrees and 40 degrees. That is, the pain due to the rubbing of the bones on the inner leg side of the knee joint appears most remarkably when the knee joint angle is between 20 degrees and 40 degrees. Therefore, according to the above configuration, the pain due to the rubbing of the bones on the inner leg side of the knee joint can be efficiently reduced.

The knee brace may be configured so that the extended state of the knee joint is not released by a ground reaction force when a diseased leg to which the knee brace is attached contacts the ground. According to the above configuration, the extended state of the knee joint is not released when the diseased leg contacts the ground.

The coupling part may include: a cam groove provided in the upper arm or the lower arm; a long groove provided in the lower arm or the upper arm; a rotation fulcrum shaft that is provided in the upper arm or the lower arm and is slid in the long groove; and a cam shaft that is provided in the lower arm or the upper arm and is slid in the cam groove, in which, when the patient flexes his/her knee joint, the lower arm may be configured to be rotated with respect to the upper arm along with the rotation fulcrum shaft sliding in the long groove and the cam shaft sliding in the cam groove, and an area of the cam groove where the cam shaft is positioned when the knee joint is in an extended state may be orthogonal to a longitudinal direction of the upper arm, or the area of the cam groove of the outer leg joint may be inclined in such a way that it goes downward toward an end part of the cam groove on the extending side, or the area of the cam groove of the inner leg joint may be inclined in such a way that it goes upward toward the end part of the cam groove on the extending side. According to the above configuration, it is possible to achieve a configuration in which the extended state of the knee joint is not released when the diseased leg contacts the ground with the simple configuration.

An energizing part that energizes the outer leg joint and the inner leg joint in such a way that they approach each other may be further included. According to the above configuration, it is possible to prevent the inner leg joint from being distorted in the inner leg side.

A leg brace including the aforementioned knee brace may be provided.

According to the present disclosure, it is possible to prevent the shank from rotating externally with respect to the thigh when the knee joint is extended.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, with reference to the drawings, specific embodiments to which the present disclosure is applied will be described in detail. However, the present disclosure is not limited to the following embodiments. Further, the following descriptions and the drawings are simplified as appropriate for the sake of clarity of the description.

Figure 1:
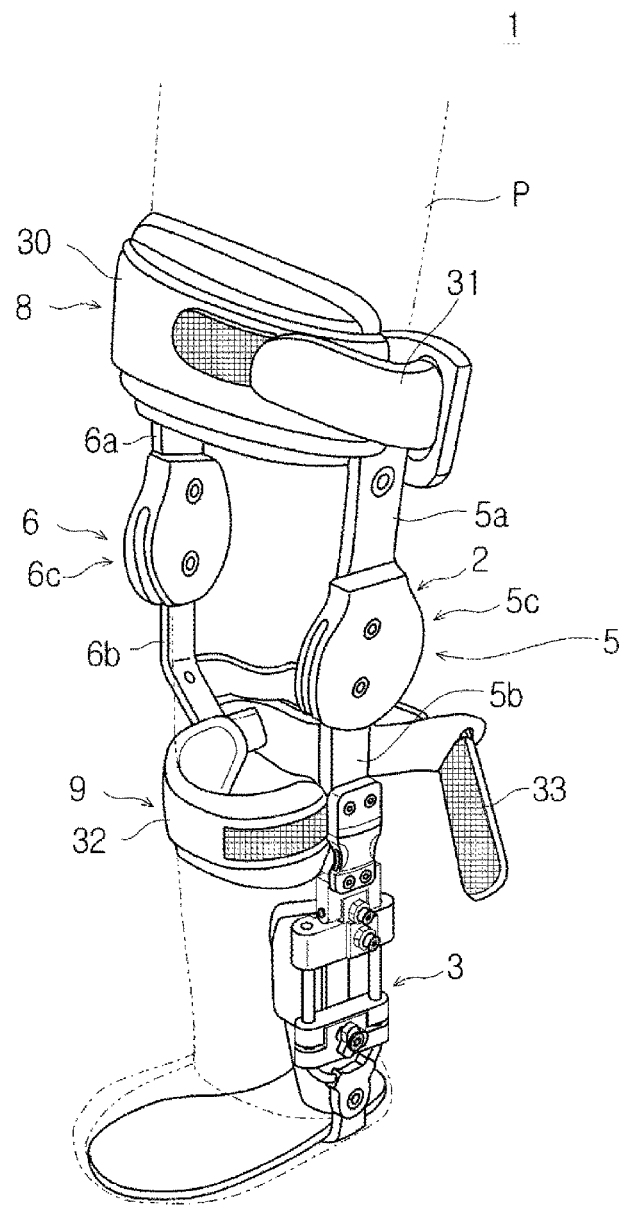
FIG. 1 is a perspective view of a leg brace.

First, a configuration of a leg brace according to this embodiment will be described. FIG. 1 is a perspective view showing a usage form of the leg brace according to this embodiment. FIG. 1 shows a shoe that a wearer wears by an alternate long and short dash line and a leg of the wearer by an alternate long and two short dashes line in order to clarify the configuration of the leg brace.

The following description illustrates a leg brace attached to the left leg of the wearer, in which a yaw axis is an axis that is extended in the vertical direction of a wearer who wears the leg brace and is in a standing posture, a roll axis is an axis that is extended in the front-back direction of the wearer who wears the leg brace and is in the standing posture, and a pitch axis is an axis that is extended in the right-left direction of the wearer who wears the leg brace and is in the standing posture. However, the yaw axis, the pitch axis, and the roll axis are defined for the sake of convenience in order to clarify the description and vary depending on the walking posture of the wearer. In the following description, the right side with respect to the left leg may be referred to as "an inner side or an inner leg side" and the left side with respect to the left leg may be referred to as "outside or an outer leg side".

As shown in FIG. 1, the leg brace 1, which is suitably attached to a leg in order to relieve a pain that a knee osteoarthritis patient having an O-leg feels in his/her knee joint, includes a knee brace 2 and a shank assisting tool 3. The knee brace 2, which is attached to the knee of the diseased leg of a wearer P (patient), is configured to be flexed following flexing of the knee joint of the wearer P. Specifically, the knee brace 2 includes a thigh fixing part 8, a shank fixing part 9, an outer leg joint 5, and an inner leg joint 6.

The thigh fixing part 8 is attached to the thigh of the wearer P.

The shank fixing part 9 is attached to the shank of the wearer P.

The outer leg joint 5 couples the thigh fixing part 8 and the shank fixing part 9, is provided in the outer leg side of the knee joint of the wearer P, and can be flexed.

The outer leg joint 5 includes an upper arm 5a, a lower arm 5b, and a coupling part 5c. The upper arm 5a is provided along a side part of the thigh. The lower arm 5b is provided along a side part of the shank. The upper arm 5a and the lower arm 5b are coupled to each other by the coupling part 5c arranged in a side part of the knee joint.

The upper arm 5a is extended in the yaw axis direction and has a plate having a long length that is substantially orthogonal to the pitch axis as its basic form. The lower arm 5b, which is also extended in the yaw axis direction, has a plate having a long length that is substantially orthogonal to the pitch axis as its basic form.

The coupling part 5c couples the lower end part of the upper arm 5a and the upper end part of the lower arm 5b in such a way that they can be rotated about the pitch axis.

Figure 2:
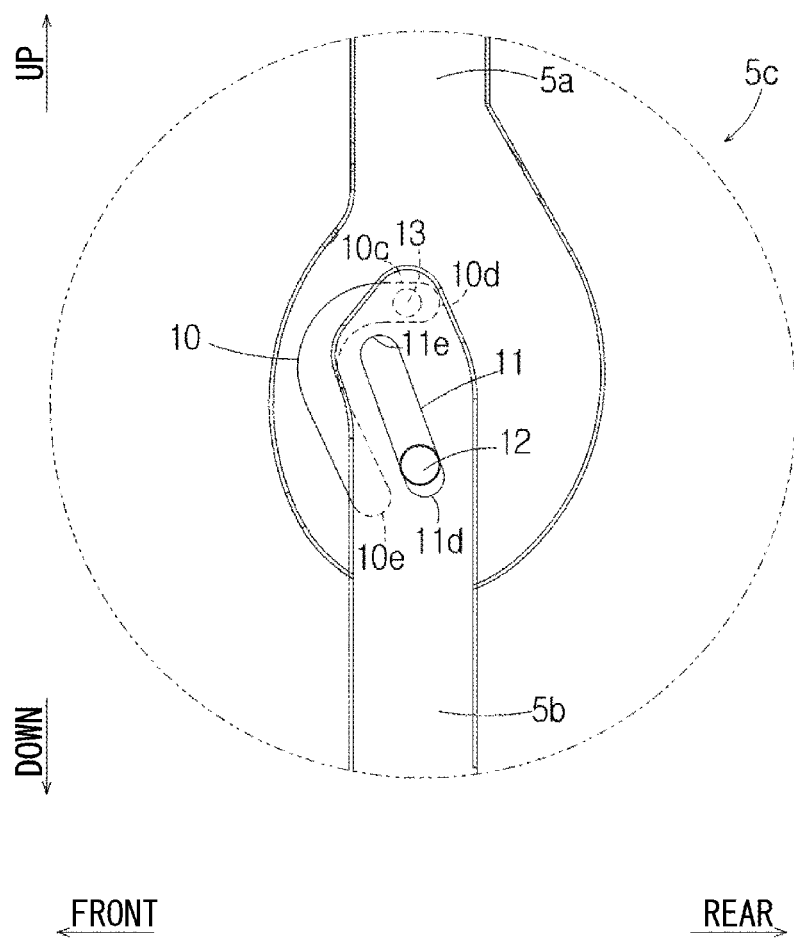
FIG. 2 is a partial side view of an outer leg joint when a knee joint angle is 0 degrees.

FIG. 2 shows the coupling part 5c of the outer leg joint 5 in the extended state. As shown in FIG. 2, the coupling part 5c is composed of a cam groove 10 provided in the upper arm 5a, a long groove 11 provided in the lower arm 5b, a rotation fulcrum shaft 12 that is provided in the upper arm 5a and is slid in the long groove 11, and a cam shaft 13 that is provided in the lower arm 5b and is slid in the cam groove 10.

When the wearer P flexes his/her knee joint, the lower arm 5b is rotated relative to the upper arm 5a along with the rotation fulcrum shaft 12 sliding in the long groove 11 and the cam shaft 13 sliding in the cam groove 10.

Referring once again to FIG. 1, the inner leg joint 6 couples the thigh fixing part 8 and the shank fixing part 9, is provided in the inner leg side of the knee joint of the wearer P, and can be flexed.

The inner leg joint 6 includes an upper arm 6a, a lower arm 6b, and a coupling part 6c. The upper arm 6a is arranged along the side part of the thigh. The lower arm 6b is arranged along the side part of the shank. The upper arm 6a and the lower arm 6b are coupled to each other at the coupling part 6c provided in the side part of the knee joint.

The upper arm 6a is extended in the yaw axis direction and has a plate having a long length that is substantially orthogonal to the pitch axis as its basic form. The lower arm 6b, which is also extended in the yaw axis direction, has a plate having a long length that is substantially orthogonal to the pitch axis as its basic form.

The coupling part 6c couples the lower end part of the upper arm 6a and the upper end part of the lower arm 6b in such a way that they can be rotated about the pitch axis.

Figure 8:
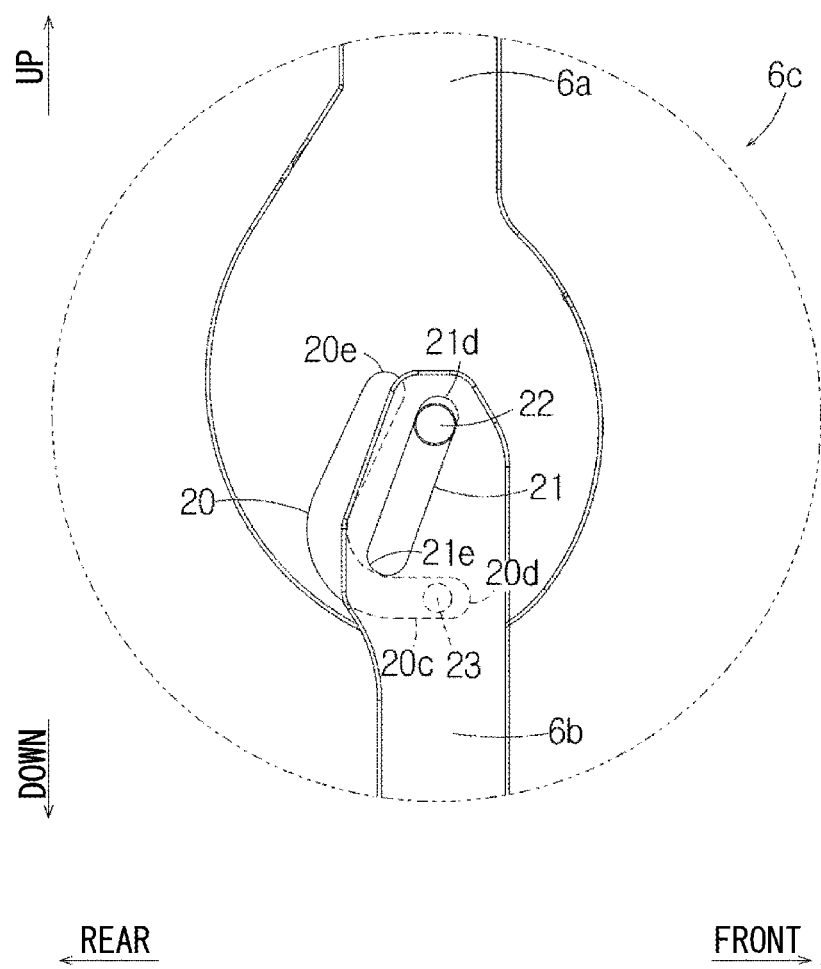
FIG. 8 is a partial side view of an inner leg joint when the knee joint angle is 0 degrees.

FIG. 8 shows the coupling part 6c of the inner leg joint 6 in the extended state. As shown in FIG. 8, the coupling part 6c is composed of a cam groove 20 provided in the upper arm 6a, a long groove 21 provided in the lower arm 6b, a rotation fulcrum shaft 22 that is provided in the upper arm 6a and is slid in the long groove 21, and a cam shaft 23 that is provided in the lower arm 6b and is slid in the cam groove 20.

When the wearer P flexes his/her knee joint, the lower arm 6b is rotated relative to the upper arm 6a along with the rotation fulcrum shaft 22 sliding in the long groove 21 and the cam shaft 23 sliding in the cam groove 20.

The coupling part 5c and the coupling part 6c will be described later in detail.

Referring once again to FIG. 1, the thigh fixing part 8 is attached to the thigh of the wearer P. The thigh fixing part 8 fixes the upper arm 5a of the outer leg joint 5 and the upper arm 6a of the inner leg joint 6 to the thigh of the wearer P. The thigh fixing part 8 includes a thigh cuff 30 and a thigh belt 31.

The thigh cuff 30 is arranged so as to be opposed to the front surface of the thigh of the wearer P. The thigh cuff 30 is curved to be convex toward the front in a plan view. The thigh cuff 30 has one end fixed to the upper end of the upper arm 5a of the outer leg joint 5 and the other end fixed to the upper end of the upper arm 6a of the inner leg joint 6.

The thigh belt 31 is wound around the thigh of the wearer P so that both the thigh of the wearer P and the thigh cuff 30 are concurrently wrapped in the thigh belt 31, whereby the thigh cuff 30 is fixed to the thigh of the wearer P.

The shank fixing part 9 is attached to the shank of the wearer P. The shank fixing part 9 fixes the lower arm 5b of the outer leg joint 5 and the lower arm 6b of the inner leg joint 6 to the shank of the wearer P. The shank fixing part 9 includes a shank cuff 32 and a shank belt 33.

The shank cuff 32 is arranged so as to be opposed to the front surface of the shank of the wearer P. The shank cuff 32 is curved to be convex toward the front in a plan view. The shank cuff 32 has one end fixed to the lower end of the lower arm 5b of the outer leg joint 5 and the other end fixed to the lower end of the lower arm 6b of the inner leg joint 6.

The shank belt 33 is wound around the shank of the wearer P so that both the shank of the wearer P and the shank cuff 32 are concurrently wrapped in the shank belt 33, whereby the shank cuff 32 is fixed to the shank of the wearer P.

According to the above structures, when the wearer P extends his/her knee with the knee brace 2 attached to his/her knee, the outer leg joint 5 and the inner leg joint 6 are extended while the knee brace 2 internally rotating the shank of the wearer P relative to the thigh. Therefore, the knee brace 2 is able to relieve a strong pain that a patient feels in his/her knee joint who is suffering from, for example, the shank over-external rotation syndrome in which the patient feels a pain in his/her knee joint due to the external rotation of the shank relative to the thigh when the knee joint is extended while the diseased leg is in the idling leg state.

The shank assisting tool 3 prevents the thrust of the knee of the wearer P. The descriptions of the shank assisting tool 3 will be omitted. The shank assisting tool 3 is configured in such a way that it can be attached to and detached from the knee brace 2.

Next, the coupling part 5c and the coupling part 6c will be described in detail. Hereinafter, the description of the structures of the coupling part 5c and the coupling part 6c will be given based on the posture in which the coupling part 5c and the coupling part 6c are in the extended state and the longitudinal directions of the upper arm 5a, the lower arm 5b, the upper arm 6a, and the lower arm 6b are all parallel to the vertical direction, as shown in FIGS. 2 and 8, for the sake of convenience of the description.

(Coupling Part 5c)

As shown in FIG. 2, in this embodiment, the upper arm 5a is provided inside the lower arm 5b. Alternatively, the upper arm 5a may be arranged outside of the lower arm 5b.

Figure 3:
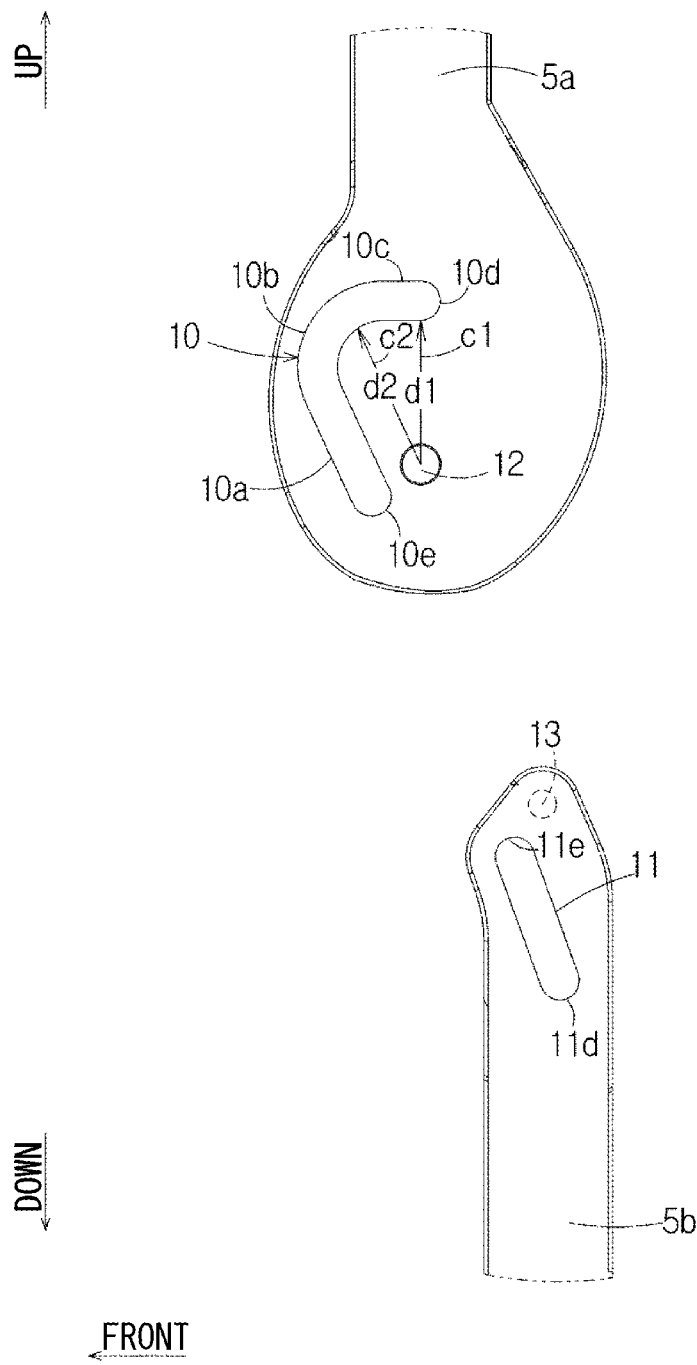
FIG. 3 is an exploded side view of the outer leg joint.

FIG. 3 shows a state in which the upper arm 5a is removed from the lower arm 5b and the upper arm 5a and the lower arm 5b are separated from each other in the vertical direction for the sake of convenience of the description.

As shown in FIG. 3, the cam groove 10 and the rotation fulcrum shaft 12 are formed in the upper arm 5a.

The cam groove 10 is curved and extended so as to be convex toward the front and upward. Specifically, the cam groove 10 includes a flexing-side cam groove 10a, an intermediate cam groove 10b, and an extending-side cam groove 10c. The intermediate cam groove 10b forms an acute angle between the flexing-side cam groove 10a and the extending-side cam groove 10c. The flexing-side cam groove 10a, the intermediate cam groove 10b, and the extending-side cam groove 10c are successively formed in this order in the clockwise direction in a side view in which the coupling part 5c is seen from the outer leg side.

The flexing-side cam groove 10a is linearly extended and is inclined with respect to the longitudinal direction of the upper arm 5a in such a way that it extends upward as it extends forward.

The intermediate cam groove 10b is extended in an arc shape from the upper end of the flexing-side cam groove 10a and is curved so as to be convex toward the front and upward.

The extending-side cam groove 10c, which is linearly extended from the rear end of the intermediate cam groove 10b, is extended so as to be parallel to the front-back direction. That is, the extending-side cam groove 10c is extended so as to be orthogonal to the longitudinal direction of the upper arm 5a.

The rotation fulcrum shaft 12 is a shaft that serves as a fulcrum of the rotation of the lower arm 5b. The rotation fulcrum shaft 12 is arranged below the extending-side cam groove 10c. The rotation fulcrum shaft 12 is arranged behind the flexing-side cam groove 10a. The rotation fulcrum shaft 12 is arranged outside of the area surrounded by the cam groove 10. The rotation fulcrum shaft 12 may be the one in which a metallic shaft is attached to the upper arm 5a or may be the one injection-molded along with the upper arm 5a.

An auxiliary line c1 that is parallel to the vertical direction is drawn from the center of the rotation fulcrum shaft 12 toward the extending-side cam groove 10c, and a distance d1 from the center of the rotation fulcrum shaft 12 to the extending-side cam groove 10c on the auxiliary line c1 is defined. Further, an auxiliary line c2 that is inclined with respect to the vertical direction by 20 degrees is drawn toward the intermediate cam groove 10b from the center of the rotation fulcrum shaft 12, and a distance d2 from the center of the rotation fulcrum shaft 12 to the intermediate cam groove 10b on the auxiliary line c2 is defined. In this embodiment, the relationship: distance d2>distance d1 is established. Further, the distance from the center of the rotation fulcrum shaft 12 to the intermediate cam groove 10b is the largest on the auxiliary line c2.

The cam groove 10 includes an extending-side end part 10d and a flexing-side end part 10e. Both the extending-side end part 10d and the flexing-side end part 10e are end parts of the cam groove 10 in the longitudinal direction. The extending-side end part 10d is an end part that the cam shaft 13 of the lower arm 5b approaches when the outer leg joint 5 is extended. The flexing-side end part 10e is an end part that the cam shaft 13 of the lower arm 5b approaches when the outer leg joint 5 is flexed.

The long groove 11 is linearly extended and is inclined with respect to the vertical direction in such a way that it extends upward as it extends forward. The long groove 11 includes an extending-side end part 11d and a flexing-side end part 11e. The extending-side end part 11d, which is an end part of the long groove 11 in its lower end, is an end part that the rotation fulcrum shaft 12 of the upper arm 5a approaches when the outer leg joint 5 is extended. The flexing-side end part 11e, which is an end part of the long groove 11 in its upper end, is an end part that the rotation fulcrum shaft 12 of the upper arm 5a approaches when the outer leg joint 5 is flexed.

The cam shaft 13 is arranged above the long groove 11. The cam shaft 13 is arranged above and behind the flexing-side end part 11e of the long groove 11. The cam shaft 13 is arranged above and in front of the extending-side end part 11d of the long groove 11. The cam shaft 13 may be the one in which a metallic shaft is attached to the lower arm 5b or may be the one injection-molded along with the lower arm 5b.

(Coupling Part 6c)

As shown in FIG. 8, in this embodiment, the upper arm 6a is arranged outside of the lower arm 6b. The upper arm 6a may instead be arranged in the inner side of the lower arm 6b.

Figure 9:
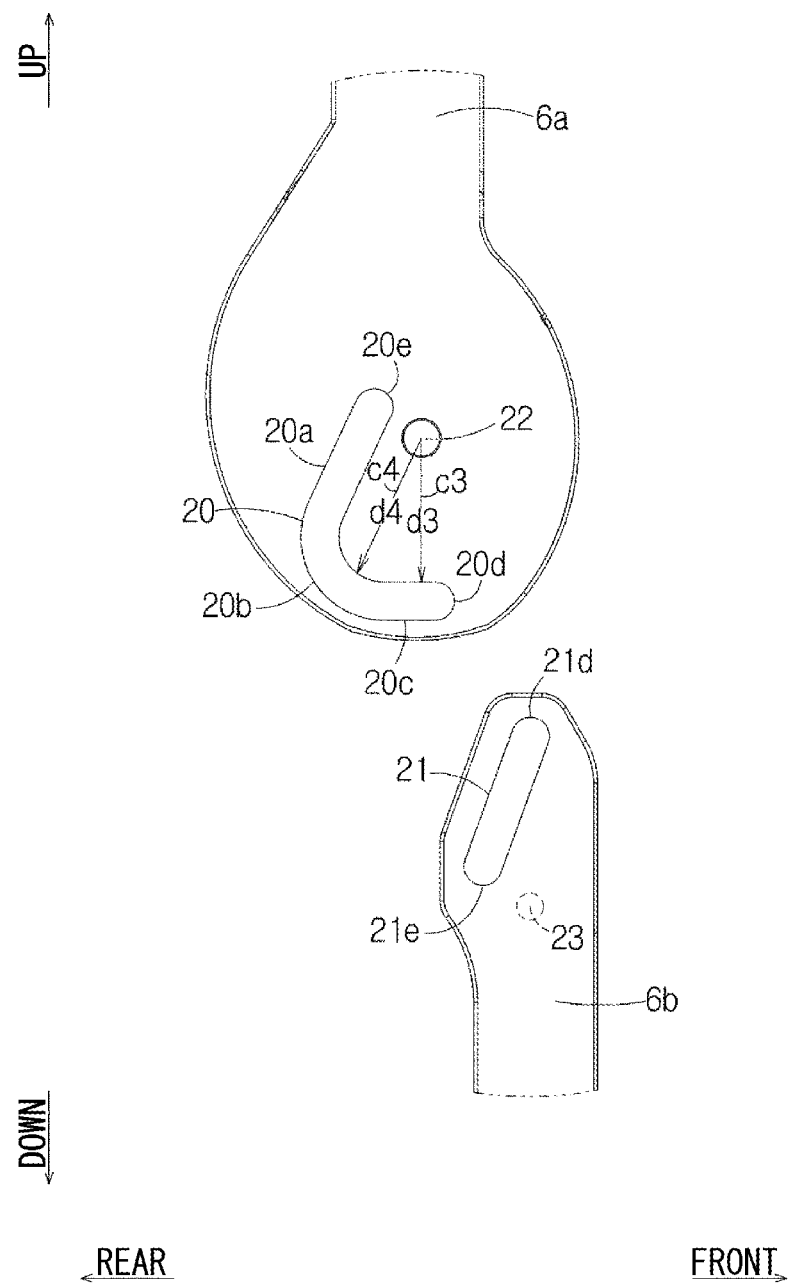
FIG. 9 is an exploded side view of an inner leg joint.

FIG. 9 shows a state in which the upper arm 6a is removed from the lower arm 6b and the upper arm 6a and the lower arm 6b are separated from each other in the vertical direction for the sake of convenience of the description.

As shown in FIG. 9, the cam groove 20 and the rotation fulcrum shaft 22 are formed in the upper arm 6a.

The cam groove 20 is curved and extended so as to be convex toward the rear side and downward. Specifically, the cam groove 20 includes a flexing-side cam groove 20a, an intermediate cam groove 20b, and an extending-side cam groove 20c. The intermediate cam groove 20b forms an acute angle between the flexing-side cam groove 20a and the extending-side cam groove 20c. The flexing-side cam groove 20a, the intermediate cam groove 20b, and the extending-side cam groove 20c are successively formed in this order in the counterclockwise direction in a side view in which the coupling part 6c is seen from the inner leg side.

The flexing-side cam groove 20a, which is linearly extended, is inclined with respect to the longitudinal direction of the upper arm 6a so that it extends downward as it extends rearward.

The intermediate cam groove 20b, which is extended in an arc shape from the lower end of the flexing-side cam groove 20a, is curved so as to be convex toward the rear side and downward.

The extending-side cam groove 20c, which is linearly extended from the front end of the intermediate cam groove 20b, is extended in such a way that it becomes parallel to the front-back direction. That is, the extending-side cam groove 20c is extended in such a way that it is orthogonal to the longitudinal direction of the upper arm 6a.

The rotation fulcrum shaft 22 is a shaft that serves as a fulcrum of the rotation of the lower arm 6b. The rotation fulcrum shaft 22 is arranged above the extending-side cam groove 20c. The rotation fulcrum shaft 22 is arranged in the front of the flexing-side cam groove 20a. The rotation fulcrum shaft 22 is arranged outside of the area surrounded by the cam groove 20. The rotation fulcrum shaft 22 may be the one in which a metallic shaft is attached to the upper arm 6a or may be the one injection-molded along with the upper arm 6a.

An auxiliary line c3 that is parallel to the vertical direction is drawn toward the extending-side cam groove 20c from the center of the rotation fulcrum shaft 22, and a distance d3 from the center of the rotation fulcrum shaft 22 to the extending-side cam groove 20c on the auxiliary line c3 is defined. Further, an auxiliary line c4 that is inclined with respect to the vertical direction by 20 degrees is drawn toward the intermediate cam groove 20b from the center of the rotation fulcrum shaft 22, and the distance d4 from the center of the rotation fulcrum shaft 22 to the intermediate cam groove 20b on the auxiliary line c4 is defined. In this embodiment, the relationship: distance d4>distance d3 is established. Further, the distance from the center of the rotation fulcrum shaft 22 to the intermediate cam groove 20b is the largest on the auxiliary line c4.

The cam groove 20 includes an extending-side end part 20d and a flexing-side end part 20e. Both the extending-side end part 20d and the flexing-side end part 20e are end parts of the cam groove 20 in the longitudinal direction. The extending-side end part 20d is an end part that the cam shaft 23 of the lower arm 6b approaches when the inner leg joint 6 is extended. The flexing-side end part 20e is an end part that the cam shaft 23 of the lower arm 6b approaches when the inner leg joint 6 is flexed.

The long groove 21 is linearly extended and is inclined with respect to the vertical direction in such a way that it extends upward as it extends forward. The long groove 21 includes an extending-side end part 21d and a flexing-side end part 21e. The extending-side end part 21d, which is an end part of the long groove 21 in its upper end, is an end part that the rotation fulcrum shaft 22 of the upper arm 6a approaches when the inner leg joint 6 is extended. The flexing-side end part 21e, which is an end part of the long groove 21 in its lower end, is an end part that the rotation fulcrum shaft 22 of the upper arm 6a approaches when the inner leg joint 6 is flexed.

The cam shaft 23 is arranged below the long groove 21. The cam shaft 23 is arranged below and in the front of the flexing-side end part 21e of the long groove 21. The cam shaft 23 is arranged below the extending-side end part 21d of the long groove 21. The cam shaft 23 may be the one in which a metallic shaft is attached to the lower arm 6b or may be the one injection-molded along with the lower arm 6b.

Next, an operation of the leg brace 1 will be described. In the following description, the positions where the rotation fulcrum shaft 12, the cam shaft 13, the rotation fulcrum shaft 22, and the cam shaft 23 are provided for each knee joint angle will be mainly described.

(Knee Joint Angle=0 Degrees)
(Outer Leg Joint 5)

As shown in FIG. 2, when the knee joint angle is 0 degrees, that is, when the knee joint is in the extended state, the rotation fulcrum shaft 12 is positioned in the extending-side end part 11d of the long groove 11. Further, the cam shaft 13 is located in the extending-side cam groove 10c of the cam groove 10, and specifically, located in the extending-side end part 10d.

As described above, when the knee joint angle is 0 degrees, the cam shaft 13 is positioned in the extending-side cam groove 10c of the cam groove 10, and the extending-side cam groove 10c is extended in such a way that it is orthogonal to the longitudinal direction of the upper arm 5a. This prevents the cam shaft 13 from moving in a direction away from the extending-side end part 10d of the cam groove 10 due to the ground reaction force that the diseased leg to which the knee brace 2 is attached receives when it contacts the ground. Therefore, when the diseased leg to which the knee brace 2 is attached contacts the ground, the extended state of the outer leg joint 5 is maintained.

(Inner Leg Joint 6)

As shown in FIG. 8, when the knee joint angle is 0 degrees, that is, when the knee joint is in the extended state, the rotation fulcrum shaft 22 is positioned in the extending-side end part 21d of the long groove 21. Further, the cam shaft 23 is positioned in the extending-side cam groove 20c of the cam groove 20, and specifically, positioned in the extending-side end part 20d.

As described above, when the knee joint angle is 0 degrees, the cam shaft 23 is positioned in the extending-side cam groove 20c of the cam groove 20 and the extending-side cam groove 20c is extended in such a way that it is orthogonal to the longitudinal direction of the upper arm 6a. This prevents the cam shaft 23 from moving in a direction away from the extending-side end part 20d of the cam groove 20 due to the ground reaction force that the diseased leg to which the knee brace 2 is attached receives when it contacts the ground. Therefore, when the diseased leg to which the knee brace 2 is attached contacts the ground, the extended state of the inner leg joint 6 is maintained.

(Knee Joint Angle=30 Degrees)
(Outer Leg Joint 5)

Figure 4:
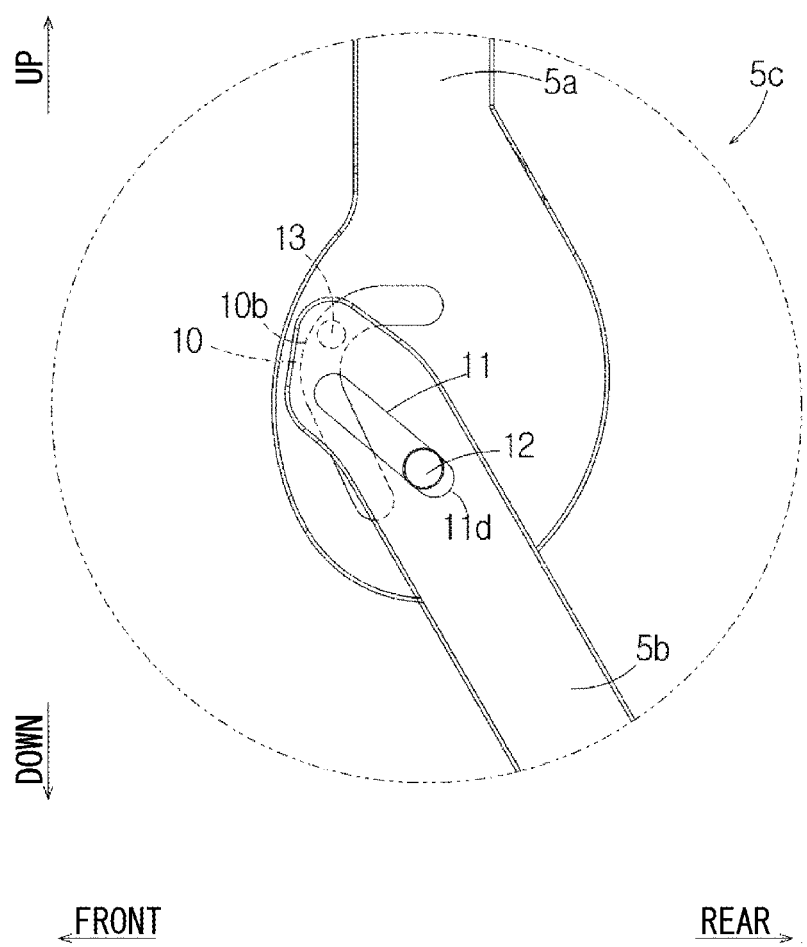
FIG. 4 is a partial side view of the outer leg joint when the knee joint angle is 30 degrees.

As shown in FIG. 4, when the knee joint angle is 30 degrees, the cam shaft 13 is positioned in the intermediate cam groove 10b of the cam groove 10. Further, the rotation fulcrum shaft 12 further slightly approaches the extending-side end part 11d of the long groove 11 compared to the case in which the knee joint angle is 0 degrees. This is because, as shown in FIG. 3, the intermediate cam groove 10b is formed away from the rotation fulcrum shaft 12 more than the extending-side cam groove 10c is, that is, because distance d2>distance d1 is established.

(Inner Leg Joint 6)

Figure 10:
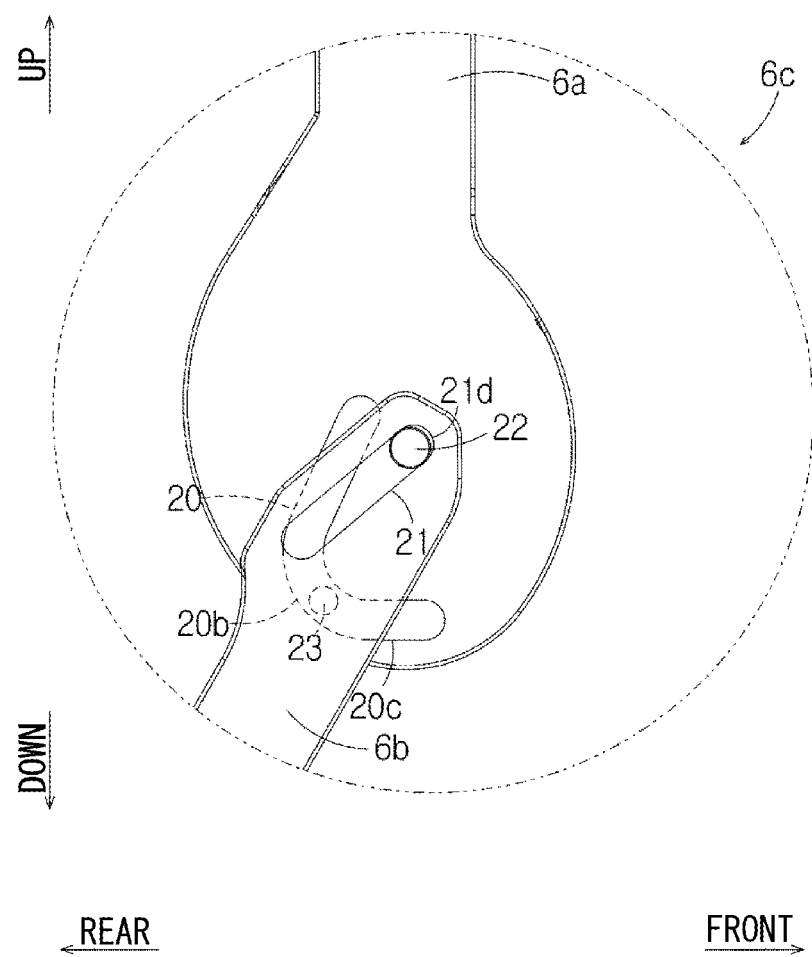
FIG. 10 is a partial side view of the inner leg joint when the knee joint angle is 30 degrees.

As shown in FIG. 10, when the knee joint angle is 30 degrees, the cam shaft 23 is positioned in the intermediate cam groove 20b of the cam groove 20. Further, the rotation fulcrum shaft 22 further slightly approaches the extending-side end part 21d of the long groove 21 compared to the case in which the knee joint angle is 0 degrees. This is because, as shown in FIG. 9, the intermediate cam groove 20b is formed away from the rotation fulcrum shaft 22 more than the extending-side cam groove 20c is, that is, because distance d4>distance d3 is established.

(Knee Joint Angle=60 Degrees)

(Outer Leg Joint 5)

Figure 5:
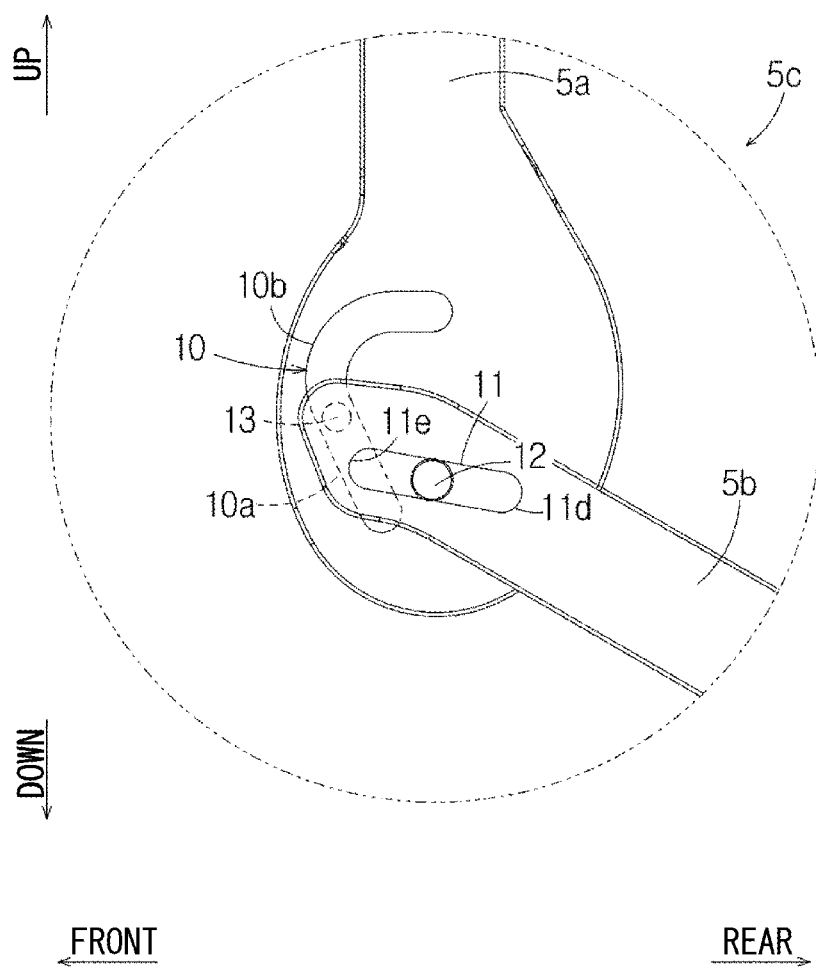
FIG. 5 is a partial side view of the outer leg joint when the knee joint angle is 60 degrees.

As shown in FIG. 5, when the knee joint angle is 60 degrees, the rotation fulcrum shaft 12 is positioned in the center of the long groove 11 in the longitudinal direction. Further, the cam shaft 13 is positioned in the vicinity of the boundary between the flexing-side cam groove 10a and the intermediate cam groove 10b of the cam groove 10.

(Inner Leg Joint 6)

Figure 11:
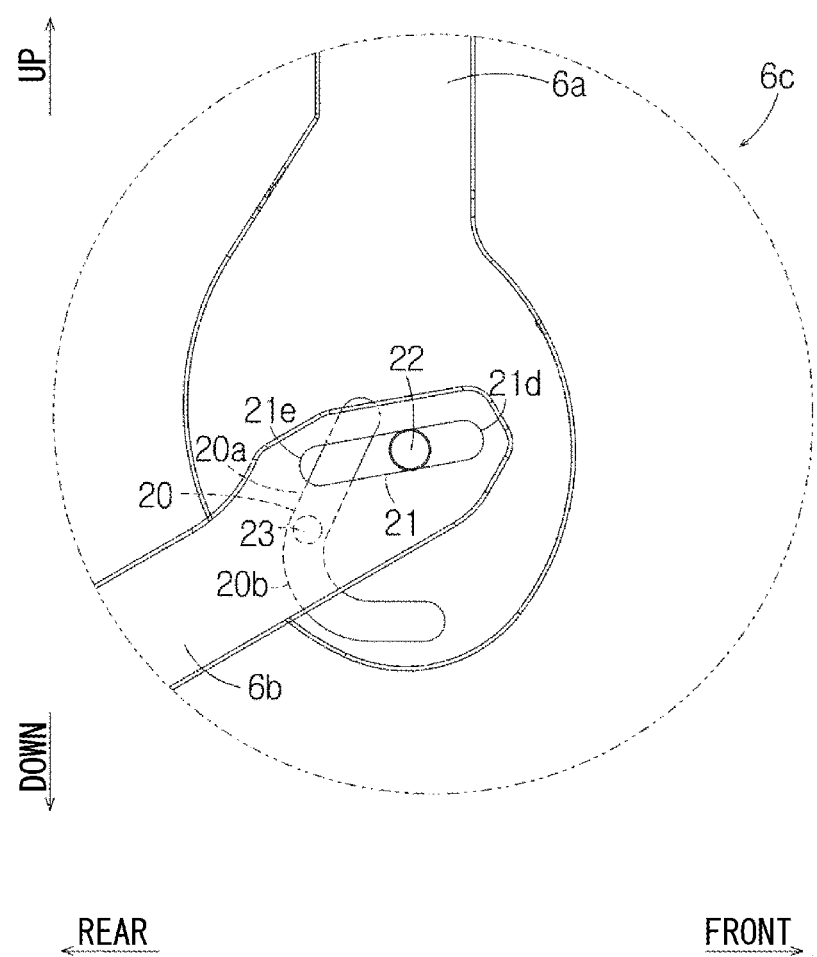
FIG. 11 is a partial side view of the inner leg joint when the knee joint angle is 60 degrees.

As shown in FIG. 11, when the knee joint angle is 60 degrees, the rotation fulcrum shaft 22 is positioned in the center of the long groove 21 in the longitudinal direction. Further, the cam shaft 23 is positioned in the vicinity of the boundary between the flexing-side cam groove 20a and the intermediate cam groove 20b of the cam groove 20.

(Knee Joint Angle=90 Degrees)

(Outer Leg Joint 5)

Figure 6:
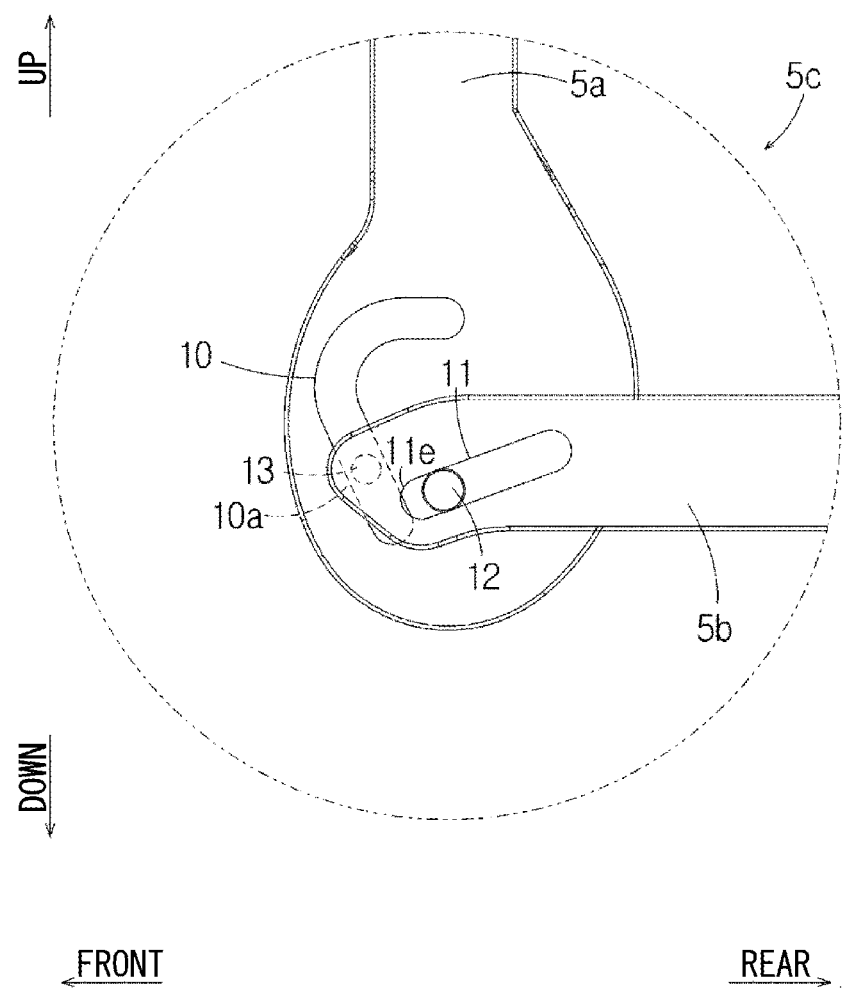
FIG. 6 is a partial side view of the outer leg joint when the knee joint angle is 90 degrees.

As shown in FIG. 6, when the knee joint angle is 90 degrees, the rotation fulcrum shaft 12 is positioned in the vicinity of the flexing-side end part 11e of the long groove 11. Further, the cam shaft 13 is positioned in the flexing-side cam groove 10a of the cam groove 10, and specifically, positioned in the center of the flexing-side cam groove 10a in the longitudinal direction.

(Inner Leg Joint 6)

Figure 12:
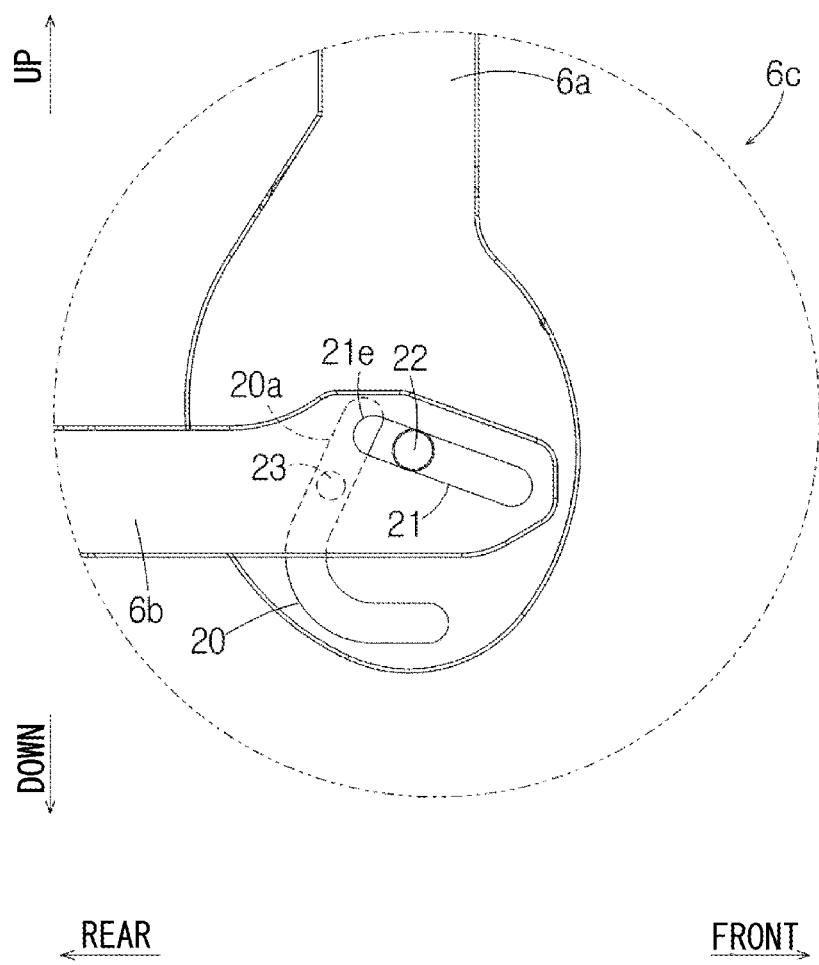
FIG. 12 is a partial side view of the inner leg joint when the knee joint angle is 90 degrees.

As shown in FIG. 12, when the knee joint angle is 90 degrees, the rotation fulcrum shaft 22 is positioned in the vicinity of the flexing-side end part 21e of the long groove 21. Further, the cam shaft 23 is positioned in the flexing-side cam groove 20a of the cam groove 20, and specifically, positioned in the center of the flexing-side cam groove 20a in the longitudinal direction.

(Knee Joint Angle=120 Degrees)

(Outer Leg Joint 5)

Figure 7:
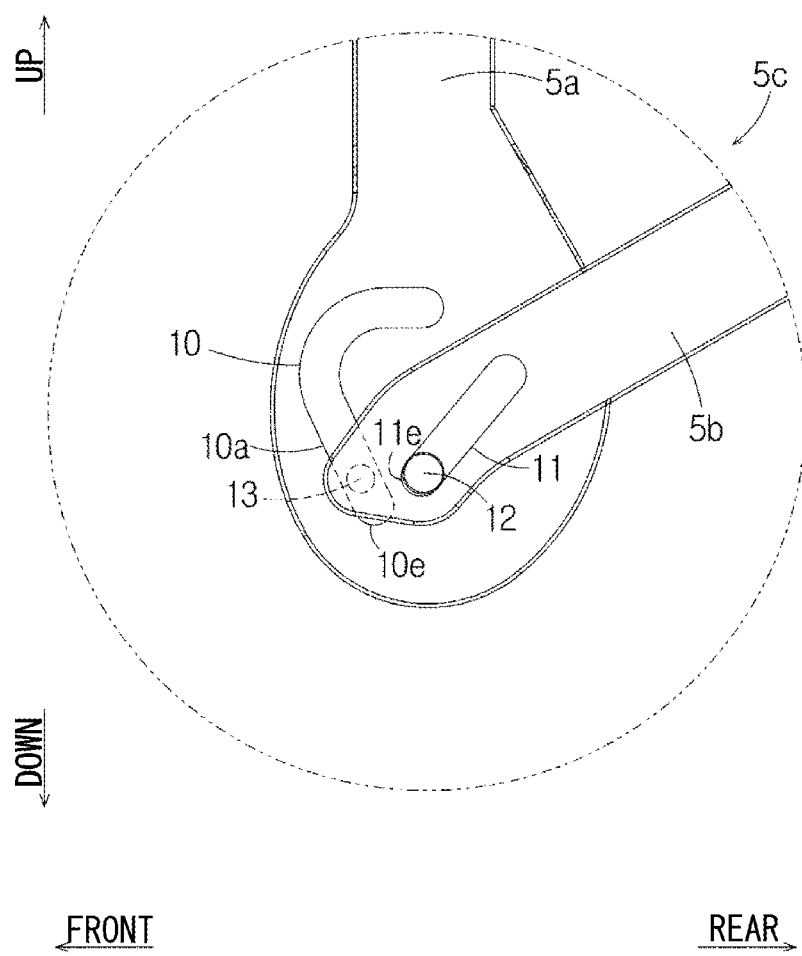
FIG. 7 is a partial side view of the outer leg joint when the knee joint angle is 120 degrees.

As shown in FIG. 7, when the knee joint angle is 120 degrees, the rotation fulcrum shaft 12 is positioned in the flexing-side end part 11e of the long groove 11. Further, the cam shaft 13 is positioned in the flexing-side cam groove 10a of the cam groove 10, and specifically, positioned in the vicinity of the flexing-side end part 10e.

(Inner Leg Joint 6)

Figure 13:
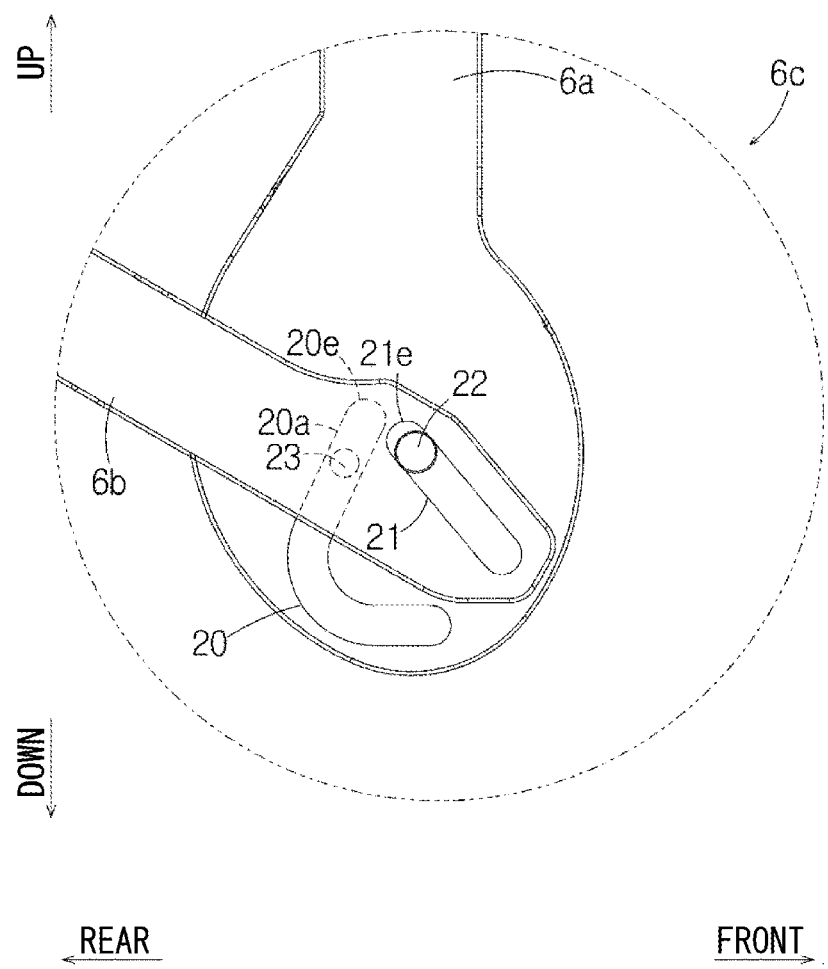
FIG. 13 is a partial side view of the inner leg joint when the knee joint angle is 120 degrees.

As shown in FIG. 13, when the knee joint angle is 120 degrees, the rotation fulcrum shaft 22 is positioned in the flexing-side end part 21e of the long groove 21. Further, the cam shaft 23 is positioned in the flexing-side cam groove 20a of the cam groove 20, and specifically, positioned in the vicinity of the flexing-side end part 20e.

As described above, when the knee joint is extended, in the outer leg joint 5 shown in FIG. 2, the cam shaft 13 moves toward the extending-side end part 10d from the flexing-side end part 10e of the cam groove 10 and the rotation fulcrum shaft 12 moves toward the extending-side end part 11d from the flexing-side end part 11e of the long groove 11.

Likewise, when the knee joint is extended, in the inner leg joint 6 shown in FIG. 8, the cam shaft 23 moves toward the extending-side end part 20d from the flexing-side end part 20e of the cam groove 20 and the rotation fulcrum shaft 22 moves toward the extending-side end part 21d from the flexing-side end part 21e of the long groove 21.

On the other hand, when the knee joint is flexed, in the outer leg joint 5 shown in FIG. 2, the cam shaft 13 moves toward the flexing-side end part 10e from the extending-side end part 10d of the cam groove 10 and the rotation fulcrum shaft 12 moves toward the flexing-side end part 11e from the extending-side end part 11d of the long groove 11. Likewise, when the knee joint is flexed, in the inner leg joint 6 shown in FIG. 8, the cam shaft 23 moves toward the flexing-side end part 20e from the extending-side end part 20d of the cam groove 20 and the rotation fulcrum shaft 22 moves toward the flexing-side end part 21e from the extending-side end part 21d of the long groove 21.

(Shank Internal Rotation Effect)

Incidentally, as shown in FIG. 2, the long groove 11 is inclined with respect to the longitudinal direction of the upper arm 5a in such a way that it extends upward as it extends forward. Then the rotation fulcrum shaft 12 is positioned in the extending-side end part 11d when the knee joint is in the extended state and the rotation fulcrum shaft 12 is positioned in the flexing-side end part 11e when the knee joint is in the flexed state. That is, when the knee joint is extended, the rotation fulcrum shaft 12 moves toward the extending-side end part 11d from the flexing-side end part 11e. In other words, when the knee joint is extended, the lower arm 5b is rotated about the rotation fulcrum shaft 12 and the lower arm 5b moves substantially forward with respect to the rotation fulcrum shaft 12 by the amount of the deviation between the extending-side end part 11d and the flexing-side end part 11e in the front-back direction.

Likewise, as shown in FIG. 8, the long groove 21 is inclined with respect to the longitudinal direction of the upper arm 6a in such a way that it extends upward as it extends forward. Then the rotation fulcrum shaft 22 is positioned in the extending-side end part 21d when the knee joint is in the extended state and the rotation fulcrum shaft 22 is positioned in the flexing-side end part 21e when the knee joint is in the flexed state. That is, when the knee joint is extended, the rotation fulcrum shaft 22 moves toward the extending-side end part 21d from the flexing-side end part 21e. In other words, when the knee joint is extended, the lower arm 6b is rotated about the rotation fulcrum shaft 22 and the lower arm 6b is moved substantially rearward with respect to the rotation fulcrum shaft 22 by the amount of the deviation between the extending-side end part 21d and the flexing-side end part 21e in the front-back direction.

As described above, when the knee joint is extended, the lower arm 5b is be moved forward relative to the upper arm 5a in the outer leg joint 5, and the lower arm 6b is moved relatively backward with respect to the upper arm 6a in the inner leg joint 6. In other words, when the knee joint is extended, the lower arm 5b is be moved forward relative to the lower arm 6b and the lower arm 6b is moved relatively backward with respect to the lower arm 5b. Accordingly, the shank is caused to be internally rotated with respect to the thigh. Therefore, when the patient feels a pain in his/her knee joint due to the external rotation of the shank with respect to the thigh when the knee joint is extended, this pain can be relieved by preventing this external rotation.

Figure 14:
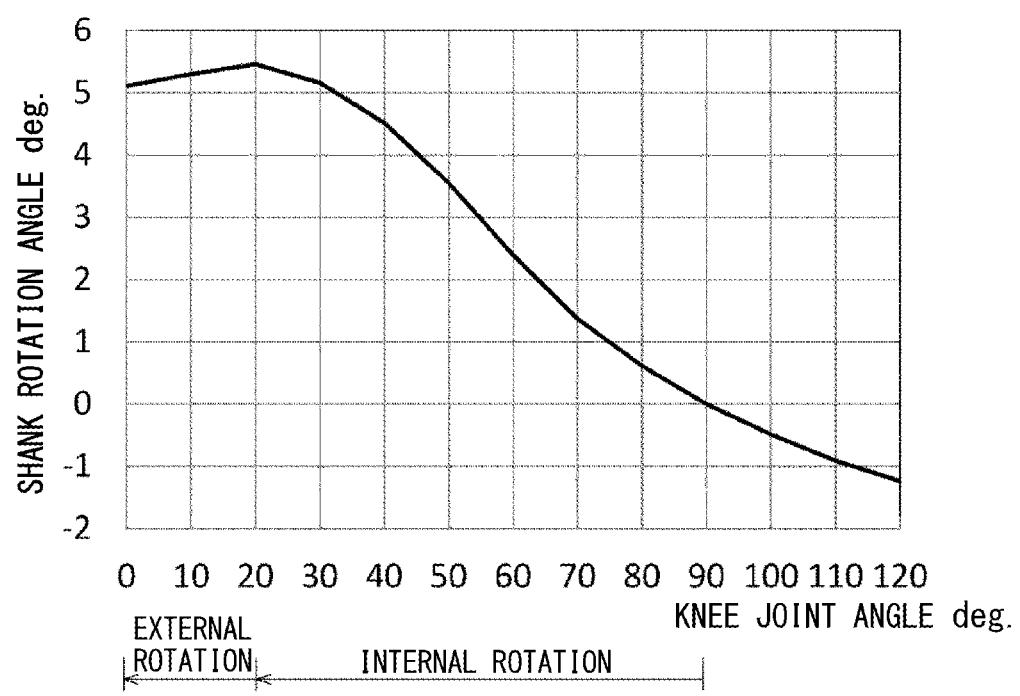
FIG. 14 is a graph showing a relationship between a knee joint angle and a shank rotation angle.

FIG. 14 shows a graph of the shank internal rotation effect exerted by the knee brace 2 according to this embodiment. As shown in FIG. 14, in this embodiment, as one example, when the knee joint is extended and the knee joint angle goes from 90 degrees to 20 degrees, the shank acts to be rotated internally with respect to the thigh. When the knee joint is further extended and the knee joint angle goes from 20 degrees to 0 degrees, the shank acts to be rotated externally with respect to the thigh. This is because the establishment of the relationship distance d2>distance d1 makes the rotation fulcrum shaft 12 slightly return toward the flexing-side end part 11e just before the knee joint reaches the extended state, as shown in FIG. 3, and the establishment of the relationship distance d4>distance d3 makes the rotation fulcrum shaft 22 slightly return toward the flexing-side end part 21e just before the knee joint reaches the extended state, as shown in FIG. 9. As described above, the shank is slightly rotated externally with respect to the thigh just before the completion of the extension of the knee joint, whereby it is possible to reproduce the screw-home movement.

Figure 15:
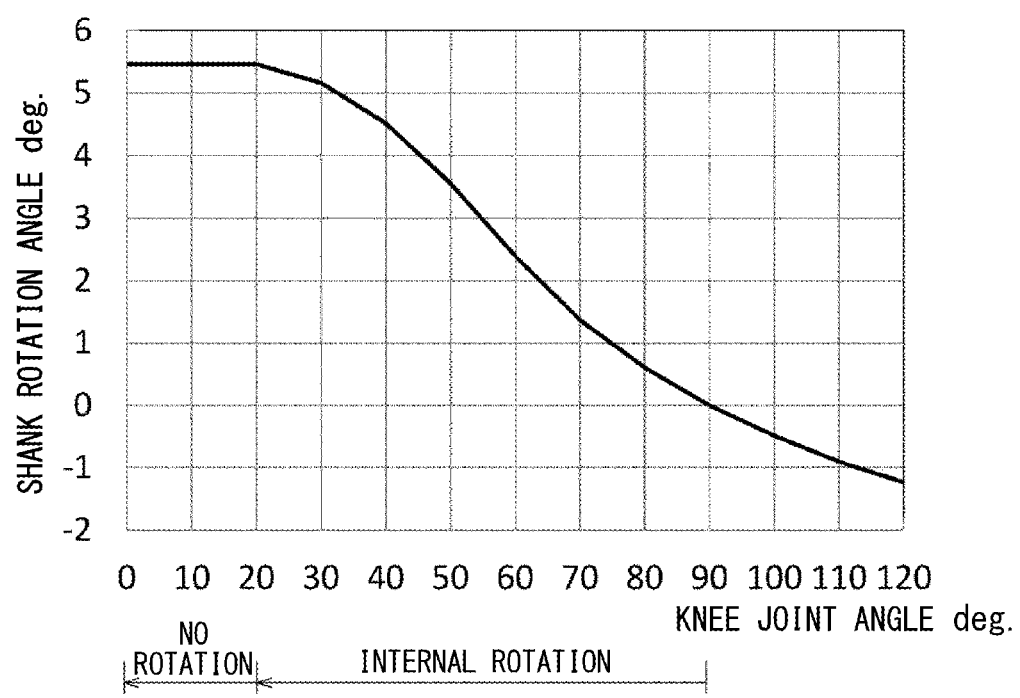
FIG. 15 is a graph showing a relationship between a knee joint angle and a shank rotation angle according to a first modified example.
Figure 16:
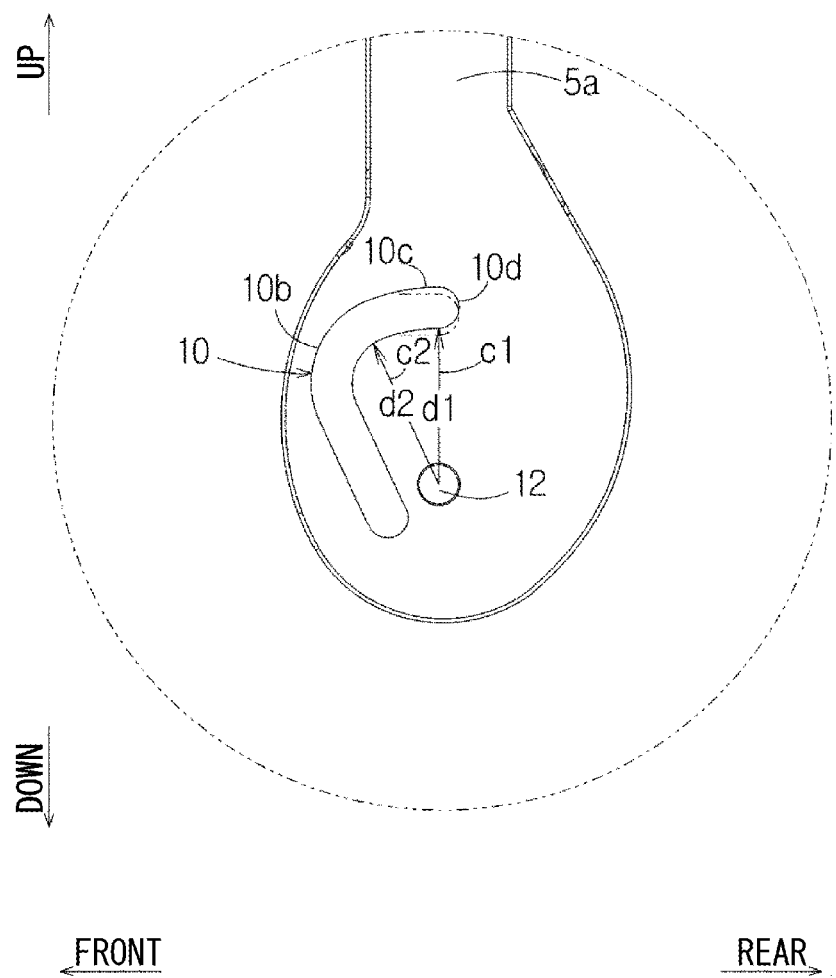
FIG. 16 is a side view of an upper arm of the outer leg joint according to the first modified example.
Figure 17:
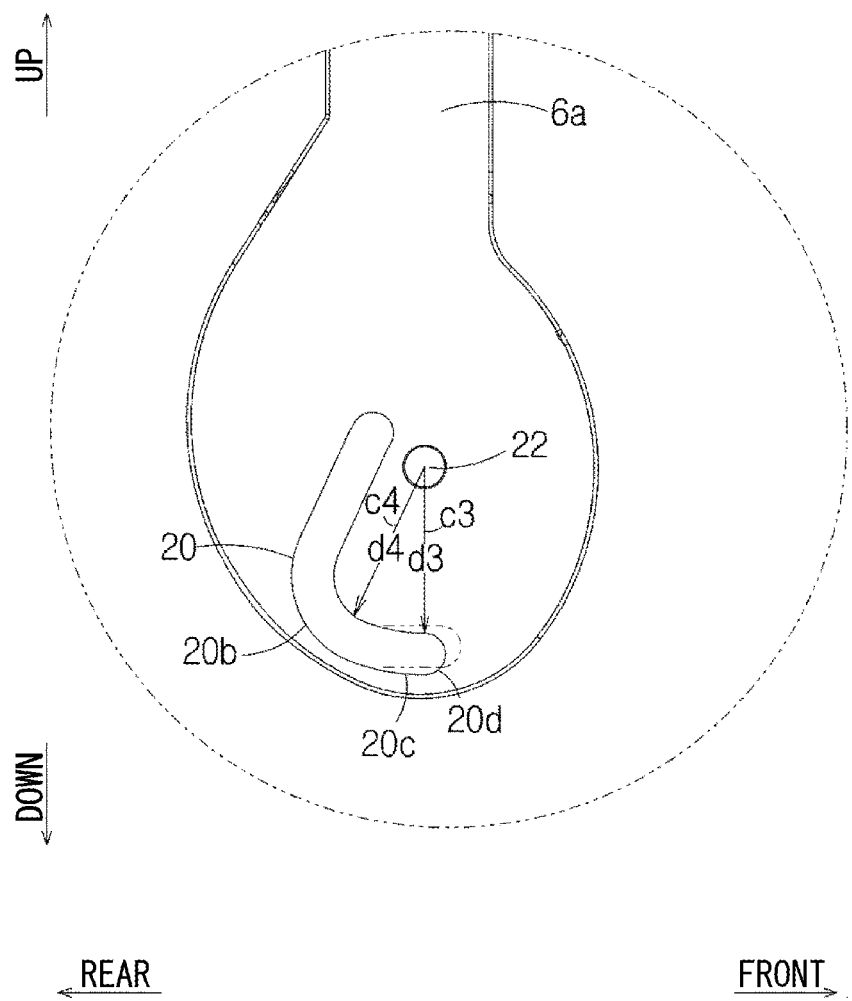
FIG. 17 is a side view of an upper arm of the inner leg joint according to the first modified example

However, as shown in FIG. 15, for example, the shank may not be rotated with respect to the thigh while the knee joint angle goes from 20 degrees to 0 degrees. Specifically, the extending-side cam groove 10c is formed to draw an arc around the rotation fulcrum shaft 12 in such a way that distance d2=distance d1, as shown in FIG. 16, and the extending-side cam groove 20c is formed to draw an arc around the rotation fulcrum shaft 22 in such a way that distance d4=distance d3, as shown in FIG. 17. According to this configuration, while the knee joint angle goes from 20 degrees to 0 degrees, the rotation fulcrum shaft 12 does not move in the long groove 11 and the rotation fulcrum shaft 22 does not move in the long groove 21. Therefore, the shank is not rotated with respect to the thigh.

Figure 18:
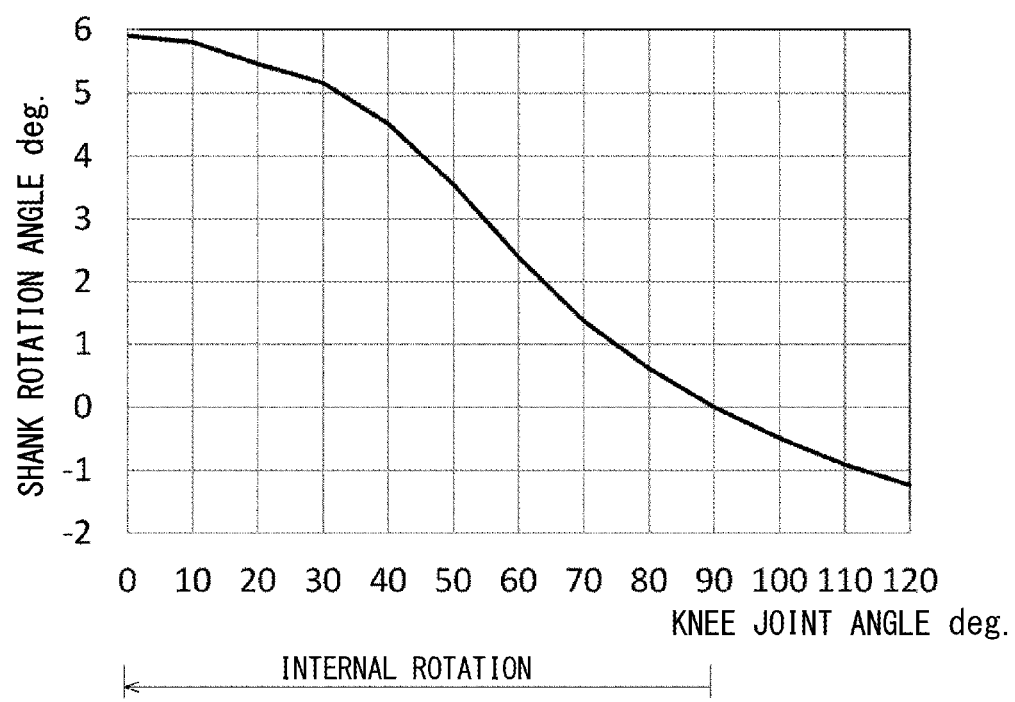
FIG. 18 is a graph showing a relationship between a knee joint angle and a shank rotation angle according to a second modified example.
Figure 19:
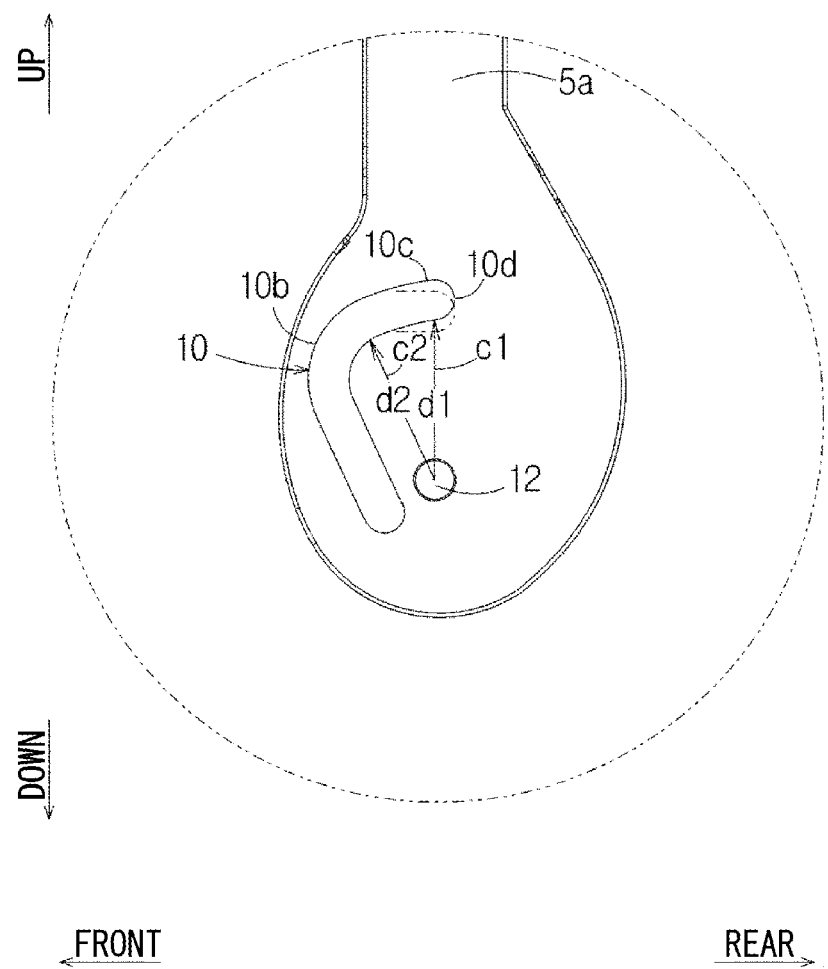
FIG. 19 is a side view of an upper arm of an outer leg joint according to the second modified example.
Figure 20:
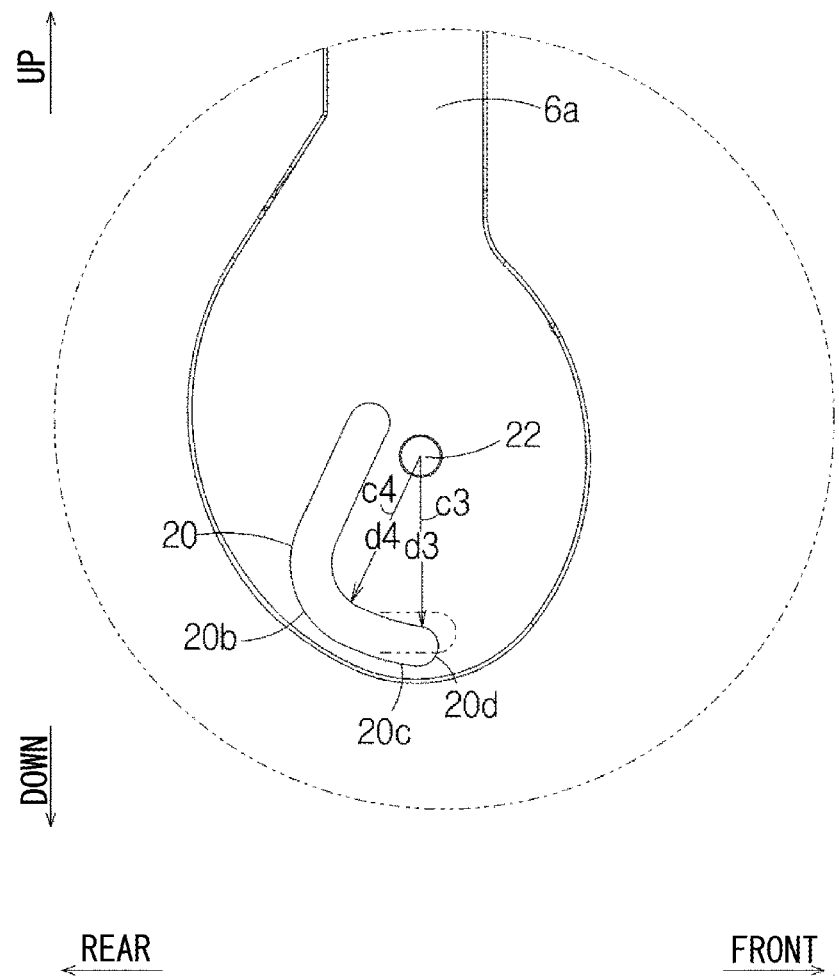
FIG. 20 is a side view of an upper arm of an inner leg joint according to the second modified example.

Further, as shown in FIG. 18, for example, the shank may be rotated further internally with respect to the thigh while the knee joint angle goes from 20 degrees to 0 degrees. Specifically, the extending-side cam groove 10c is formed in such a way that it is away from the rotation fulcrum shaft 12 toward the extending-side end part 10d in such a way that distance d2<distance d1, as shown in FIG. 19, and the extending-side cam groove 20c is formed in such a way that it is away from the rotation fulcrum shaft 22 toward the extending-side end part 20d in such a way that distance d4<distance d3, as shown in FIG. 20. According to this configuration, while the knee joint angle goes from 20 degrees to 0 degrees, the rotation fulcrum shaft 12 is further moved toward the extending-side end part 11d in the long groove 11, and the rotation fulcrum shaft 22 is further moved toward the extending-side end part 21d in the long groove 21. Therefore, the shank is rotated internally continuously with respect to the thigh.

(Varus Relief Effect)

Further, as shown in FIG. 2, the long groove 11 is inclined with respect to the upper arm 5a in such a way that it extends upward as it extends forward. Then the rotation fulcrum shaft 12 is positioned in the extending-side end part 11d when the knee joint is in the extended state and the rotation fulcrum shaft 12 is positioned in the flexing-side end part 11e when the knee joint is in the flexed state. That is, when the knee joint is extended, the rotation fulcrum shaft 12 moves toward the extending-side end part 11d from the flexing-side end part 11e.

In other words, when the knee joint is extended, the lower arm 5b is moved substantially upward by the amount of deviation between the extending-side end part 11d and the flexing-side end part 11e in the vertical direction. In other words, when the knee joint is extended, the distance between the rotation fulcrum shaft 12 and the shank fixing part 9 becomes short.

Likewise, as shown in FIG. 8, the long groove 21 is inclined with respect to the upper arm 6a in such a way that it extends upward as it extends forward. Then the rotation fulcrum shaft 22 is positioned in the extending-side end part 21d when the knee joint is in the extended state, and the rotation fulcrum shaft 22 is positioned in the flexing-side end part 21e when the knee joint is in the flexed state. That is, when the knee joint is extended, the rotation fulcrum shaft 22 moves toward the extending-side end part 21d from the flexing-side end part 21e. In other words, when the knee joint is extended, the lower arm 6b is moved substantially downward by the amount of the deviation between the extending-side end part 21d and the flexing-side end part 21e in the vertical direction. In other words, when the knee joint is extended, the distance between the rotation fulcrum shaft 22 and the shank fixing part 9 becomes long.

As described above, when the knee joint is extended, the lower arm 5b moves relatively upward with respect to the upper arm 5a in the outer leg joint 5 and the lower arm 6b moves relatively downward with respect to the upper arm 6a in the inner leg joint 6. In other words, when the knee joint is extended, the lower arm 5b moves relatively upward with respect to the lower arm 6b and the lower arm 6b moves relatively downward with respect to the lower arm 5b. That is, when the knee joint is extended, the distance between the rotation fulcrum shaft 12 and the shank fixing part 9 becomes short and the distance between the rotation fulcrum shaft 22 and the shank fixing part 9 becomes long. Accordingly, the knee joint is pressed toward the inner leg side when the knee joint is extended, whereby it is possible to relieve the pain due to the rubbing of the bones on the inner leg side of the knee joint.

Further, the rotation fulcrum shaft 12 approaches the extending-side end part 11d the most when the knee joint angle is 20 degrees. This is because, as shown in FIG. 3, the cam groove 10 is the farthest from the rotation fulcrum shaft 12 in the auxiliary line c2 that is inclined with respect to the auxiliary line c1 by 20 degrees. As described above, in this embodiment, at a stage before the completion of the extension of the outer leg joint 5, that is, when, for example, the knee joint angle is 20 degrees, the lower arm 5b of the outer leg joint 5 is configured to move relatively most upward with respect to the lower arm 6b of the inner leg joint 6. In other words, when the knee joint is extended in the case in which the knee joint angle is 20 degrees, the distance between the rotation fulcrum shaft 12 and the shank fixing part 9 becomes the shortest and the distance between the rotation fulcrum shaft 22 and the shank fixing part 9 becomes the longest. According to the above configuration, the following effects may be obtained.

That is, the present inventors have found that the pain due to the rubbing of the bones on the inner leg side of the knee joint appears most remarkably at a stage before the completion of the extension of the outer leg joint 5. Therefore, according to the above configuration, the pain due to the rubbing of the bones on the inner leg side of the knee joint can be efficiently reduced.

In this embodiment, when the knee joint angle is 20 degrees, the lower arm 5b of the outer leg joint 5 is configured to move relatively most upward with respect to the lower arm 6b of the inner leg joint 6. As described above, the timing when the lower arm 5b of the outer leg joint 5 is moved relatively most upward with respect to the lower arm 6b of the inner leg joint 6 is not limited to a timing when the knee joint angle is 20 degrees. That is, when the knee joint angle is a desired angle between 20 degrees to 40 degrees, the lower arm 5*b* of the outer leg joint 5 may move relatively most upward with respect to the lower arm 6*b* of the inner leg joint 6. It is assumed here that the joint angle of the knee joint when the outer leg joint 5 is extended is 0 degrees and the joint angle increases in the positive direction when the outer leg joint 5 is flexed.

In this embodiment, when the knee joint is extended in the case in which the knee joint angle is 20 degrees, the distance between the rotation fulcrum shaft 12 and the shank fixing part 9 becomes the shortest and the distance between the rotation fulcrum shaft 22 and the shank fixing part 9 becomes the longest. As described above, the timing when the distance between the rotation fulcrum shaft 12 and the shank fixing part 9 becomes the shortest and the distance between the rotation fulcrum shaft 22 and the shank fixing part 9 becomes the longest is not limited to the case in which the knee joint angle is 20 degrees. That is, when the knee joint angle is a desired angle between 20 degrees to 40 degrees, the distance between the rotation fulcrum shaft 12 and the shank fixing part 9 may become the shortest and the distance between the rotation fulcrum shaft 22 and the shank fixing part 9 may become the longest.

The aforementioned varus relief effect is exerted also in the inner leg joint 6. However, since the description of the inner leg joint 6 is similar to that of the outer leg joint 5, the description will be omitted.

Figure 21:
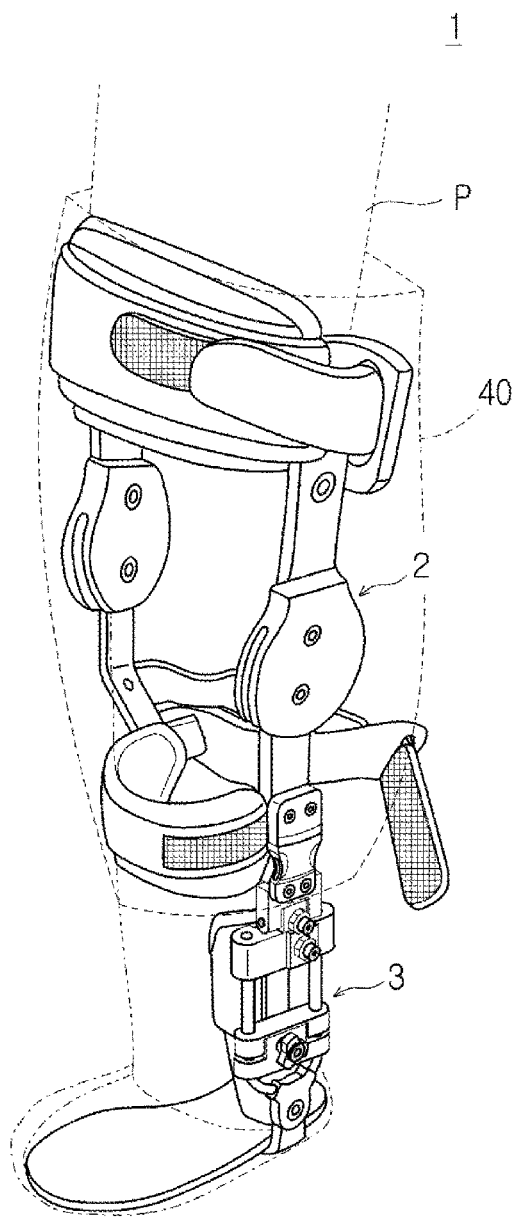
FIG. 21 is a perspective view of a leg brace covered with a cylindrical body.

Incidentally, the knee brace 2 may further include an energizing part that energizes the outer leg joint 5 and the inner leg joint 6 so that they approach each other. As shown in FIG. 21, the energizing part, which is, for example, a cylindrical body 40 having stretchability, is used to cover the knee brace 2. According to the above configuration, it is possible to prevent the inner leg joint 6 from being distorted in the inner leg side.

That is, since the joint motions of the knee joints are complicated, it is practically impossible for the coupling part 5*c* of the outer leg joint 5 and the coupling part 6*c* of the inner leg joint 6 to completely follow the joint motions. Therefore, it may be possible that, when the knee joint is flexed, the outer leg joint 5 may be bent toward the outer leg side and the inner leg joint 6 may be bent toward the inner leg side so as to absorb the inconsistency between the joint motion of the knee joint and the flexing motion of the outer leg joint 5 and the inner leg joint 6. When, for example, the knee brace 2 is attached to both legs, the inner leg joint 6 which is on the right leg side and the inner leg joint 6 which is on the left leg side may collide with each other when the patient walks, which may cause damage to the inner leg joints 6. With the aforementioned energizing part, it is possible to prevent the inner leg joints 6 from bending toward the inner leg side, as a result of which it is possible to increase the life of the knee brace 2.

The embodiments of the present application have been described above. The above embodiments have the following features.

The knee brace 2 for the knee osteoarthritis patient includes the thigh fixing part 8 that is attached to the thigh of the wearer P, the shank fixing part 9 that is attached to the shank of the patient, the outer leg joint 5 that couples the thigh fixing part 8 with the shank fixing part 9, is provided on the outer leg side of the knee joint of the wearer P, and can be flexed, and the inner leg joint 6 that couples the thigh fixing part 8 with the shank fixing part 9, is provided on the inner leg side of the knee joint of the wearer P, and can be flexed. The outer leg joint 5 and the inner leg joint 6 respectively include the upper arms 5*a* and 6*a* provided along the side part of the thigh and the lower arms 5*b* and 6*b* provided along the side part of the shank. The upper arm 5*a* and the lower arm 5*b* are coupled to each other by the coupling part 5*c* provided in the side part of the knee joint. The upper arm 6*a* and the lower arm 6*b* are coupled to each other by the coupling part 6*c* provided in the side part of the knee joint. When the outer leg joint 5 and the inner leg joint 6 are extended, the lower arm 5*b* of the outer leg joint 5 is configured to be moved relatively forward with respect to the lower arm 6*b* of the inner leg joint 6.

According to the above configuration, the knee brace 2 operates to internally rotate the shank with respect to the thigh when the knee joint is extended. Therefore, it is possible to prevent the shank from being rotated externally with respect to the thigh when the knee joint is extended. Further, since it is possible to prevent the shank from being rotated externally with respect to the thigh, the effect that the moment arm of the knee joint is reduced and the varus moment is reduced is exerted.

The coupling part 5*c* includes the cam groove 10 provided in the upper arm 5*a*, the long groove 11 provided in the lower arm 5*b*, the rotation fulcrum shaft 12 that is provided in the upper arm 5*a* and is slid in the long groove 11, and the cam shaft 13 that is provided in the lower arm 5*b* and is slid in the cam groove 10. When the wearer P flexes his/her knee joint, the lower arm 5*b* is rotated with respect to the upper arm 5*a* along with the rotation fulcrum shaft 12 sliding in the long groove 11 and the cam shaft 13 sliding in the cam groove 10. However, the coupling part 5*c* may include the cam groove 10 provided in the lower arm 5*b*, the long groove 11 provided in the upper arm 5*a*, the rotation fulcrum shaft 12 that is provided in the lower arm 5*b* and is slid in the long groove 11, and the cam shaft 13 that is provided in the upper arm 5*a* and is slid in the cam groove 10. In this case, for example, the position, the shape and the like of the cam groove 10 are, for example, adjusted as appropriate.

The coupling part 6*c* includes the cam groove 20 provided in the upper arm 6*a*, the long groove 21 provided in the lower arm 6*b*, the rotation fulcrum shaft 22 that is provided in the upper arm 6*a* and is slid in the long groove 21, and the cam shaft 23 that is provided in the lower arm 6*b* and is slid in the cam groove 20. When the wearer P flexes his/her knee joint, the lower arm 6*b* is rotated with respect to the upper arm 6*a* along with the rotation fulcrum shaft 22 sliding in the long groove 21 and the cam shaft 23 sliding in the cam groove 20. However, the coupling part 6*c* may include the cam groove 20 provided in the lower arm 6*b*, the long groove 21 provided in the upper arm 6*a*, the rotation fulcrum shaft 22 that is provided in the lower arm 6*b* and is slid in the long groove 21, and the cam shaft 23 that is provided in the upper arm 6*a* and is slid in the cam groove 20. In this case, the position, the shape and the like of the cam groove 20 are, for example, adjusted as appropriate.

The long groove 11 of the lower arm 5*b* of the outer leg joint 5 is inclined with respect to the longitudinal direction of the lower arm 5*b* in such a way that the extending-side end part 11*d*, which is the end part of the long groove 11 where the rotation fulcrum shaft 12 is provided when the outer leg joint 5 is extended, is positioned behind the wearer P. The long groove 21 of the lower arm 6*b* of the inner leg joint 6 is inclined with respect to the longitudinal direction of the lower arm 6*b* in such a way that the extending-side end part 21*d*, which is the end part of the long groove 21 where the rotation fulcrum shaft 22 is provided when the inner leg joint 6 is extended, is positioned in front of the wearer P. According to the above configuration, the configuration in which the shank is rotated internally with respect to the thigh when the knee joint is extended is achieved with the simple configuration.

When the outer leg joint 5 and the inner leg joint 6 are extended, the distance from the rotation fulcrum shaft 12 of the outer leg joint 5 to the shank fixing part 9 becomes short and the distance from the rotation fulcrum shaft 22 of the inner leg joint 6 to the shank fixing part 9 becomes long. When the outer leg joint 5 and the inner leg joint 6 are extended, the distance from the rotation fulcrum shaft 12 of the outer leg joint 5 to the part where the lower arm 5b and the shank fixing part 9 are coupled to each other becomes short and the distance from the rotation fulcrum shaft 22 of the inner leg joint 6 to the part where the lower arm 6b and the shank fixing part 9 are coupled to each other becomes long. According to the above configuration, the knee joint is pressed toward the inner leg side when the knee joint is extended, whereby it is possible to relieve the pain due to the rubbing of the bones on the inner leg side of the knee joint.

In a case in which the rotation fulcrum shaft 12 is provided in the lower arm 5b and the rotation fulcrum shaft 22 is provided in the lower arm 6b as described above, when the outer leg joint 5 and the inner leg joint 6 are extended, the distance from the rotation fulcrum shaft 12 of the outer leg joint 5 to the thigh fixing part 8 becomes short and the distance from the rotation fulcrum shaft 22 of the inner leg joint 6 to the thigh fixing part 8 becomes long.

At the stage before the extension of the outer leg joint 5 and the inner leg joint 6 is completed, the distance between the rotation fulcrum shaft 12 of the outer leg joint 5 to the shank fixing part 9 becomes the shortest and the distance from the rotation fulcrum shaft 22 of the inner leg joint 6 to the shank fixing part 9 becomes the longest. At the stage before the extension of the outer leg joint 5 and the inner leg joint 6 is completed, the distance from the rotation fulcrum shaft 12 of the outer leg joint 5 to the part where the lower arm 5b and the shank fixing part 9 are coupled to each other becomes the shortest and the distance from the rotation fulcrum shaft 22 of the inner leg joint 6 to the part where the lower arm 6b and the shank fixing part 9 are coupled to each other becomes the longest. That is, the pain due to the rubbing of the bones on the inner leg side of the knee joint appears most remarkably at the stage before the extension of the outer leg joint 5 and the inner leg joint 6 is completed. Therefore, according to the above configuration, the pain due to the rubbing of the bones on the inner leg side of the knee joint can be efficiently reduced.

It is assumed that the knee joint angle when the outer leg joint 5 and the inner leg joint 6 are extended is 0 degrees and the knee joint angle increases in the positive direction when the outer leg joint 5 and the inner leg joint 6 are flexed. In this case, when the knee joint angle is between 20 degrees to 40 degrees, the distance from the rotation fulcrum shaft 12 of the outer leg joint 5 to the shank fixing part 9 becomes the shortest and the distance from the rotation fulcrum shaft 12 of the inner leg joint 6 to the shank fixing part 9 becomes the longest. When the knee joint angle is between 20 degrees and 40 degrees, the distance from the rotation fulcrum shaft 12 of the outer leg joint 5 to the part where the lower arm 5b and the shank fixing part 9 are coupled to each other becomes the shortest and the distance from the rotation fulcrum shaft 22 of the inner leg joint 6 to the part where the lower arm 6b and the shank fixing part 9 are coupled to each other becomes the longest. That is, the pain due to the rubbing of the bones on the inner leg side of the knee joint appears most remarkably when the knee joint angle is between 20 degrees and 40 degrees. Therefore, according to the above configuration, the pain due to the rubbing of the bones on the inner leg side of the knee joint can be efficiently reduced.

The knee brace 2 is configured in such a way that the extended state of the knee joint is not released by the ground reaction force when the diseased leg to which the knee brace 2 is attached contacts the ground. According to the above configuration, the extended state of the knee joint is not released when the diseased leg contacts the ground.

The extending-side cam groove 10c (area) of the cam groove 10 where the cam shaft 13 is positioned when the knee joint is in the extended state is orthogonal to the longitudinal direction of the upper arm 5a. Likewise, the extending-side cam groove 20c (area) of the cam groove 20 where the cam shaft 23 is positioned when the knee joint is in the extended state is orthogonal to the longitudinal direction of the upper arm 6a. According to the above configuration, it is possible to achieve the form in which the extended state of the knee joint is not released when the diseased leg contacts the ground with the simple configuration.

Note that the extending-side cam groove 10c may be inclined so as to go downward toward the extending-side end part 10d, which is the end part of the cam groove 10 on the extending side, and the extending-side cam groove 20c may be inclined so as to go upward toward the extending-side end part 20d, which is the end part of the cam groove 20 on the extending side. In this case as well, it is possible not to release the extended state of the knee joint when the diseased leg contacts the ground with the simple configuration.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A knee brace for a knee osteoarthritis patient, the knee brace comprising:
    a thigh fixing part that is configured to be attached to a thigh of a patient, the thigh fixing part including a thigh cuff and a thigh belt;
    a shank fixing part that is configured to be attached to a shank of the patient, the shank fixing part including a shank cuff and a shank belt;
    an outer leg joint that couples the thigh fixing part with the shank fixing part, is arranged in an outer leg side of a knee joint of the patient, and can be flexed; and
    an inner leg joint that couples the thigh fixing part with the shank fixing part, is arranged in an inner leg side of the knee joint of the patient, and can be flexed, wherein
    each of the outer leg joint and the inner leg joint includes a coupling part, an upper arm that is provided along a side part of the thigh and a lower arm that is provided along a side part of the shank,
    the upper arm and the lower arm of the outer leg joint are coupled to each other by the coupling part of the outer leg joint that is provided in a side part of the knee joint,
    the upper arm and the lower arm of the inner leg joint are coupled to each other by the coupling part of the inner leg joint that is provided in a side part of the knee joint,
    the lower arm of the outer leg joint is configured to be moved forward relative to the lower arm of the inner leg joint when the outer leg joint and the inner leg joint are extended, and the coupling part of each of the outer leg joint and the inner leg joint comprises a cam groove provided in one of the upper arm and the lower arm and a long groove provided in the other of the upper arm and the lower arm, the cam groove including an intermediate cam groove forming an acute angle between a flexing-side cam groove and an extending-side cam groove of the cam groove, wherein the long groove in the outer leg joint is provided rearward of the cam groove and an upper end of the long groove in the outer leg joint is provided forward of an opposite lower end of the long groove when the upper arm and the lower arm of the outer leg joint are in an extended state, wherein the long groove in the inner leg joint is provided forward of the cam groove and an upper end of the long groove in the inner leg joint is provided forward of an opposite lower end of the long groove when the upper arm and the lower arm of the outer leg joint are in an extended state.

2. The knee brace according to claim 1, wherein
the coupling part of each of the outer leg joint and the inner leg joint comprises:
a rotation fulcrum shaft that is provided in the upper arm or the lower arm and is slid in the long groove; and
a cam shaft that is provided in the lower arm or the upper arm and is slid in the cam groove, and
when the patient flexes the knee joint, the lower arm is configured to be rotated with respect to the upper arm along with the rotation fulcrum shaft sliding in the long groove and the cam shaft sliding in the cam groove.

3. The knee brace according to claim 2, wherein the coupling part of each of the outer leg joint and the inner leg joint comprises:
the cam groove is provided in the upper arm,
the long groove is provided in the lower arm,
the rotation fulcrum shaft is provided in the upper arm, and
the cam shaft is provided in the lower arm.

4. The knee brace according to claim 3, wherein
the long groove of the lower arm of the outer leg joint is inclined with respect to a longitudinal direction of the lower arm in such a way that an end part of the long groove where the rotation fulcrum shaft is provided when the outer leg joint is extended is positioned posterior with respect to a second end of the long groove, and the long groove of the lower arm of the inner leg joint is inclined with respect to the longitudinal direction of the lower arm in such a way that the end part of the long groove where the rotation fulcrum shaft is provided when the inner leg joint is extended is positioned anterior with respect to a second end of the long groove.

5. The knee brace according to claim 1, wherein the knee brace is configured so that the extended state of the knee joint is not released by a ground reaction force when a diseased leg to which the knee brace is attached contacts the ground.

6. The knee brace according to claim 1, wherein
the coupling part of each of the outer leg joint and the inner leg joint comprises:
a long groove provided in the lower arm or the upper arm;
a rotation fulcrum shaft that is provided in the upper arm or the lower arm and is slid in the long groove; and
a cam shaft that is provided in the lower arm or the upper arm and is slid in the cam groove, wherein
when the patient flexes the knee joint, the lower arm is configured to be rotated with respect to the upper arm along with the rotation fulcrum shaft sliding in the long groove and the cam shaft sliding in the cam groove, and
an area of the cam groove where the cam shaft is positioned when the knee joint is in the extended state is orthogonal to a longitudinal direction of the upper arm, or
the area of the cam groove of the outer leg joint is inclined in such a way that it goes downward toward an end part of the cam groove on the extending side, or
the area of the cam groove of the inner leg joint is inclined in such a way that it goes upward toward the end part of the cam groove on the extending side.

7. The knee brace according to claim 1, further comprising an energizing part which includes a cylindrical body that energizes the outer leg joint and the inner leg joint in such a way that they approach each other.

8. A leg brace comprising the knee brace according to claim 1.

* * * * *